(12) United States Patent
Welker et al.

(10) Patent No.: US 7,708,688 B2
(45) Date of Patent: May 4, 2010

(54) POLYMER ENDOSCOPIC SHAFT

(75) Inventors: David J. Welker, Vancouver, WA (US); Christopher D. Breckon, Vancouver, WA (US); Todd E. Holt, Vancouver, WA (US); Christopher A. Richter, Tumwater, WA (US)

(73) Assignee: Paradigm Optics, Incorporated, Vancouver, WA (US)

( * ) Notice: Subject to any disclaimer, the term of this patent is extended or adjusted under 35 U.S.C. 154(b) by 1123 days.

(21) Appl. No.: 11/080,202

(22) Filed: Mar. 14, 2005

(65) Prior Publication Data

US 2005/0203341 A1   Sep. 15, 2005

Related U.S. Application Data

(60) Provisional application No. 60/553,144, filed on Mar. 15, 2004.

(51) Int. Cl.
  *A61B 1/00* (2006.01)
  *B29D 11/00* (2006.01)
(52) U.S. Cl. .............. 600/130; 600/920; 600/128; 264/1.24
(58) Field of Classification Search .......... 600/920, 600/128, 130; 65/393; 264/1.24
  See application file for complete search history.

(56) References Cited

U.S. PATENT DOCUMENTS

| | | | |
|---|---|---|---|
| 3,742,107 A * | 6/1973 | Hawkins | 264/1.29 |
| 4,551,162 A * | 11/1985 | Hicks, Jr. | 65/393 |
| 4,812,011 A | 3/1989 | Tatsukami et al. | |
| 5,080,508 A | 1/1992 | Onishi et al. | |
| 5,148,511 A | 9/1992 | Savu et al. | |
| 5,222,180 A | 6/1993 | Kuder et al. | |
| 5,235,660 A | 8/1993 | Perry et al. | |
| 5,320,788 A * | 6/1994 | Schneider et al. | 264/1.28 |
| 5,353,365 A * | 10/1994 | Dumas et al. | 385/102 |
| 5,471,553 A * | 11/1995 | Teshima | 385/125 |
| 5,587,115 A * | 12/1996 | Allen | 264/1.24 |
| 5,593,621 A | 1/1997 | Koike et al. | |
| 5,614,253 A | 3/1997 | Nonaka et al. | |
| 5,639,512 A | 6/1997 | Nonaka et al. | |
| 5,729,645 A | 3/1998 | Garito et al. | |
| 5,747,610 A | 5/1998 | Katoot | |
| 5,756,165 A | 5/1998 | Ali et al. | |
| 5,760,139 A | 6/1998 | Koike et al. | |
| 5,851,666 A | 12/1998 | Nonaka et al. | |
| 5,861,129 A | 1/1999 | Katoot | |
| 5,869,107 A | 2/1999 | Shimizu et al. | |
| 5,881,195 A | 3/1999 | Walker | |
| 5,891,570 A | 4/1999 | Nonaka et al. | |

(Continued)

OTHER PUBLICATIONS

Kuzyk et al., "Guest-host polymer fibers for nonlinear optics", *Applied Physics Letters*, vol. 59, No. 8, pp. 902-904 (Aug. 1991).

*Primary Examiner*—John P Leubecker
(74) *Attorney, Agent, or Firm*—Townsend and Townsend and Crew LLP

(57) ABSTRACT

An endoscopic shaft having multiple endoscopic elements set in a polymer common housing. The endoscopic elements may be drawn with the common housing to manufacture a component, called an EndoFiber, which forms the length of the endoscopic shaft. A second structure, called an Endocap, may be provided that includes optical elements and which is attached to the end of the EndoFiber to form the shaft.

41 Claims, 19 Drawing Sheets

U.S. PATENT DOCUMENTS

| | | |
|---|---|---|
| 5,911,025 A | 6/1999 | Garito et al. |
| 5,916,495 A | 6/1999 | Nonaka et al. |
| 6,089,044 A | 7/2000 | Hardy et al. |
| 6,091,872 A | 7/2000 | Katoot |
| 6,154,594 A | 11/2000 | Fiacco et al. |
| 6,259,830 B1 * | 7/2001 | Bhagavatula .................... 385/2 |
| 6,322,498 B1 * | 11/2001 | Gravenstein et al. ......... 600/120 |
| 6,946,803 B2 * | 9/2005 | Moore ...................... 315/169.4 |
| 7,295,734 B2 * | 11/2007 | Bayindir et al. .............. 385/101 |
| 2003/0026995 A1 | 2/2003 | Duchesne et al. |
| 2003/0068145 A1 * | 4/2003 | Nechitailo et al. ........... 385/103 |
| 2004/0042743 A1 * | 3/2004 | Konstadinidis et al. ....... 385/100 |
| 2004/0175082 A1 * | 9/2004 | Birks et al. .................. 385/123 |
| 2005/0034484 A1 * | 2/2005 | Large et al. .................... 65/392 |
| 2007/0028651 A1 * | 2/2007 | Dowd et al. .................... 65/393 |

* cited by examiner

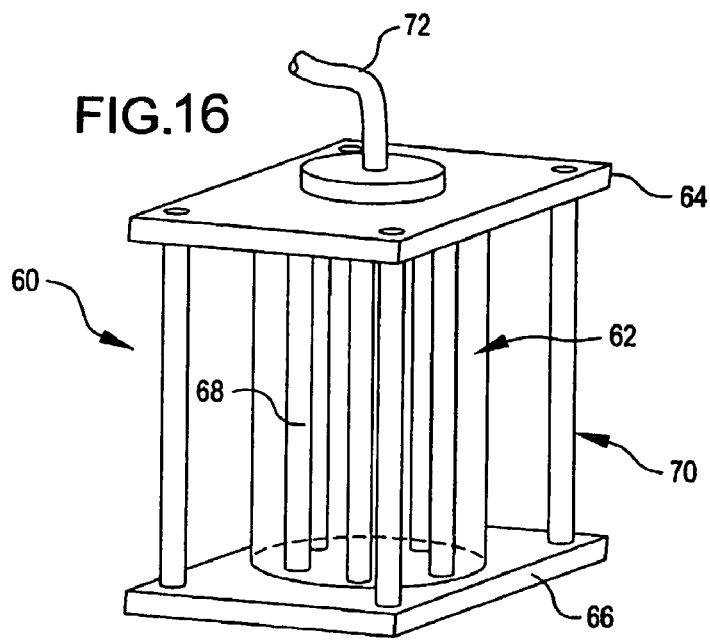
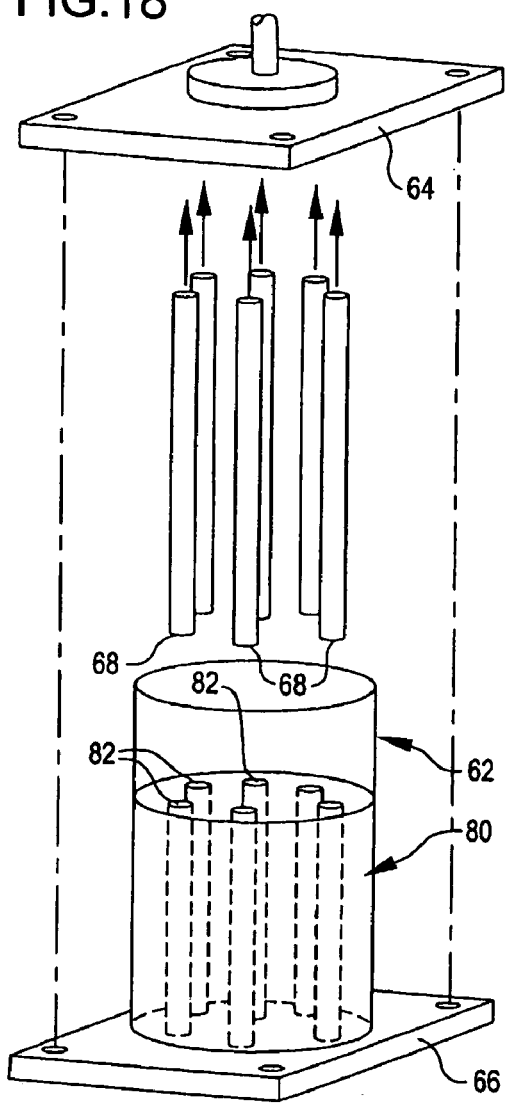
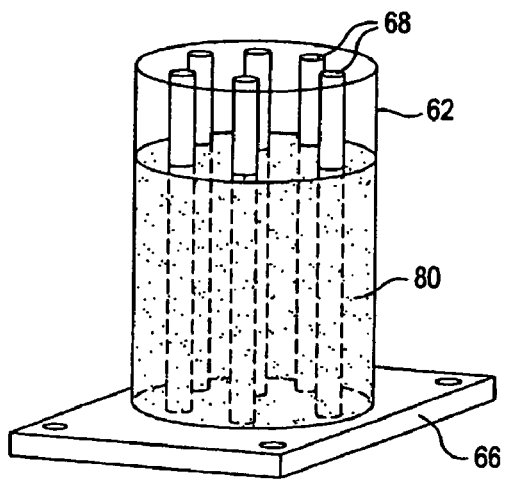

POLYMER ENDOSCOPIC SHAFT

REFERENCE TO RELATED APPLICATION

This patent application claims priority to U.S. provisional Patent Application No. 60/553,144, filed Mar. 15, 2004, and entitled "POLYMER ENDOSCOPIC SHAFT," incorporated herein by reference.

TECHNICAL FIELD OF THE INVENTION

This invention is related to endoscopes and fiberscopes, and more specifically to the shaft of an endoscope or fiberscope.

BACKGROUND OF THE INVENTION

Rapid advances in technological innovation over the past decade have transformed the average health care consumer into a buying agent with very high levels of expectation. Concurrent with this consumer trend is the trend in ever increasing health care costs and the regulatory push to contain them. Smaller, quicker, cheaper, more efficacious, and higher quality medical technologies are being sought to replace what have often been highly invasive, costly, and risky procedures in the past. In concert with this overall trend, physicians are seeking new and improved tools for gaining access to various organs and internal channels of the body with using the least invasive means possible. One such tool is the endoscope: a device used to examine and treat the interior of the body without making large incisions or without making an incision at all. Most procedures performed today using endoscopy were open surgical procedures until the equipment was developed to enable an endoscopic treatment.

An endoscope typically includes a shaft having endoscopic elements, such as imaging guides, light guides, or lumens (hollow channels) extending along its length. Contemporary fiber-based endoscopes utilize glass fibers for the imaging guides and light guides.

Current endoscopic technology is limited by a number of inherent weaknesses, which are seriously hampering the evolution in endoscopic evaluation and treatments. Some of the weaknesses associated with current endoscopes are directly linked to the use of glass fibers as endoscopic elements, and include the large size of the endoscopes, low durability, low flexibility, limited functionality, non-portability of reprocessing equipment, high cost of both the endoscope and the reprocessing equipment and, of critical importance, their non-disposability.

Large Size—A major limiting factor in many endoscopic procedures today is the size of the puncture or natural body opening, required to introduce the endoscope shaft. Reducing the size of the required opening makes it much easier on both the patient and the doctor. This also minimizes patient trauma and complications, thereby shortening the recovery time and reducing hospital cost.

Low Durability—Glass is crystalline, which makes it susceptible to fractures and breaks. Flexible glass imaging guides often have dark pixels (broken fibers) even when new; through use, more pixels go dark. Additionally, the fragile, complicated, multi-component construction of the rest of the endoscopic elements housed in the shaft and on the distal end often leads to other failures. Most breaks occur during procedures, which may cause complications, since the physician must switch endoscopes.

Low Flexibility—The bend radius of glass imaging guides is typically about three hundred times its diameter for repetitive bending. The bend radius of most materials is directly related to the size of that material. The larger diameter of the current endoscopes limits their flexibility (bend radius). High flexibility is required in many endoscopic procedures, such as examination of the biliary duct. Many applications would be easier to perform and new procedures realized by alleviating the bend limitations.

Limited Functionality—Most endoscopes are currently limited in what functions they may perform.

High Cost—Costs associated with the fabrication of an endoscope shaft are: the cost of imaging guides and light guides, the shaft housing cost, the cost of the other endoscopic elements, and the cost of assembling these components. A technology that would significantly lower cost would be very beneficial.

Non Disposable—The main reason endoscopes are not currently disposable is economic: they are just too expensive. Substantially reducing the cost of endoscopes, enabling the endoscope shaft to be disposable is desirable. There are numerous drawbacks associated with reusable endoscopes, which are described in the following paragraphs.

Patient-to-patient transfer of infections is a big problem with reusable endoscopes. There have been numerous reports and papers concerning patient-to-patient transfer of infections. In response, the CDC and FDA have issued a Public Health Advisory on this subject. An Apr. 8, 2002 article in USA Today has brought renewed public attention to this problem. The article cited and discussed several incidences of large-scale patient-to-patient transfer of infections and recent New York State Legislation action concerning endoscopes' safety.

Another problem with reusable endoscopes is staff exposure to hazardous chemicals. The chemicals used in reprocessing endoscopes, such as glutaraldehyde, may be extremely harmful to staff members. Regulations involved in working with these chemicals continue to grow more complex and elaborate.

Reusable endoscopes also have hidden costs, such as the long turnaround time between uses, and the corresponding effect on staff efficiency. Hidden costs include staff time, downtime between patients, endoscope repairs, backup endoscopes, chemicals, and cleaning equipment. These play a big part in the cost of endoscope ownership. Cleaning equipment may be difficult to operate, may not quite work right, and may leak cleaning fluid.

Repairs may be expensive on reusable endoscopes. Small flexible endoscopes break often (once during every ten procedures on average). Often the failures occur with the imaging guide (because of the fragile nature of the glass imaging guide) or other problems associated with the endoscopic elements housed in the shaft or on the distal end.

Another associated problem with reusable endoscopes is the non-portability of the components used to make the endoscopes reusable. Currently endoscopic use in the field (temporary military unit or remote hospital) is limited due to the size and the cost of equipment required to reprocess endoscopes between patients.

Reusable endoscopes also have a high cost of ownership; i.e. expense of breakage, maintenance, sterilization, risk of infection, etc. Cleaning chemicals are relatively expensive and the related equipment is very costly to purchase and maintain. For example, a STERRAD cleaning unit costs over a hundred thousand dollars to purchase. It is estimated that the cost (excluding capital equipment) of reprocessing an endoscope between patients to be $50-$150, depending on the type of endoscope.

SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In accordance with an embodiment, a polymer endoscopic shaft is provided having multiple endoscopic elements set in a single common housing structure. As used herein, such a polymer structure is referred to as an "EndoFiber." An EndoFiber endoscopic shaft provides superior properties at a lower price compared to current endoscopic shafts.

In accordance with a method of producing an EndoFiber, an EndoFiber preform is fabricated and is subsequently drawn into EndoFiber. The EndoFiber preform may be fabricated in several ways. In one method, the preform is formed by polymerizing around endoscopic elements. Another method first forms the body of the preform, containing only holes. The body of the preform is formed, for example, by extrusion, or by melt forming or polymerization around a mold with removable rods. The other elements are then inserted into the holes and the whole structure is either fused together to form the preform (which is subsequently drawn into the EndoFiber) or the structure may be vacuum drawn into the EndoFiber.

The EndoFiber may then be used as drawn or may undergo further processing to ease endoscope construction. In an embodiment, peeling or chemically etching is used to separate out the endoscopic elements from the structure to ease construction of a final device.

The number, type, and geometrical arrangement of the endoscopic elements in the EndoFiber are variable. A large variety of different polymers, thermoplastics, and/or resins may be used to manufacture the EndoFiber. In addition, the cross section of the EndoFiber and the elements contained in the EndoFiber are extremely variable, and may be, for example, a rectangle, a square, a circle, or any other suitable shape, including symmetrical and asymmetrical shapes.

Since EndoFibers may be produced as one integral unit, they reduce the total cost of endoscope manufacturing. In addition, they also increase reliability and may decrease the total endoscope shaft size if desired. As such, EndoFibers make a disposable endoscope an economically attractive alternative to reusable endoscopes. A disposable system offers a turnaround time of one-minute or less, while conventional endoscopes may require an hour or more (with cleaning and other requirements for reuse). When using a disposable system, the reprocessing cost is no longer necessary, and all of the valuable staff time spent scrubbing, rinsing, soaking and drying a conventional endoscope may be eliminated. Additionally, the costly repairs to the endoscopes are minimized.

EndoFibers in one embodiment are fabricated to make a four-way articulating micro-endoscope that is disposable. This EndoFiber is a very small four-way deflecting endoscope. The bulk of the common housing of the EndoFiber serves not only to house the other elements, but also serves to guide the illumination light. To this end, in accordance with an embodiment, the common housing is divided into quadrants, with each quadrant serving as a light guide. Each quadrant is optically isolated from the other quadrants, so that different colors (wavelengths) of light may be used. The diameter of these EndoFibers may be, for example, smaller than 0.6 mm or larger than 2 cm.

As another embodiment, an EndoFiber is provided that has two imaging guides, allowing for three-dimensional visualization. This feature provides binocular vision.

As another embodiment, an endoscope is formed of EndoFiber, with the endoscope being very small in diameter, for example less than 250 microns in diameter, with articulation and lighting functions. Such endoscopes allow direct visualization of small structures such as anatomic features in the body that have been previously difficult or impossible to view.

As another example, an EndoFiber is provided containing four imaging guides. This embodiment utilizes a different lens on the distal end for each imaging guide, which allows each guide to carry an image of an object viewed through the imaging guides with different magnification levels. As examples, standard glass lenses may be used or inexpensive plastic injected molded lenses may be used. Through proper lens design and placement, each imaging guide may have the same focal point. This would be equivalent to having a microscope with four magnification levels placed inside the body. This allows for the locating of an object macroscopically followed by inspection microscopically.

In another embodiment, an EndoFiber is provided having one central imaging guide that is forward looking and side guides, for example four side guides, that are side looking. The side guides may each have a prism attached to provide the side viewing. The imaging guides may be placed together so that the optics may be injection molded in one piece. This design allows a surgeon to view in different directions around the endoscope without bending the endoscope. The operator may, for example, view five images on five screens, all five on the same screen, or switch between views on the same screen.

In accordance with another embodiment, the polymer used for the EndoFiber is doped with a material to increase the EndoFiber's signature in an X-ray image. For example, the endoscopic shaft housing material may be doped with Barium compounds, or doping may be provided by including doped rods in the preform.

In accordance with another embodiment, a mechanism, called an EndoCap, is provided that facilitates the placement of lenses and other optics on the end of an EndoFiber. The EndoCap may be, for example, a short section of EndoFiber, having a lens and/or other optics in place of the imaging guide and/or light guides. EndoCaps may be manufactured, for example, as EndoFibers that are subsequently sliced into small sections for use, or as injection-molded parts. Examples of methods for bonding EndoCaps to EndoFibers include direct bonding, sheath-attaching, and guide pin attaching.

In accordance with another embodiment, an endoscope is provided that contains both an imaging guide and a scintillating imaging guide. This embodiment permits a doctor or other user to visually locate an object and then use X-rays or other light to obtain a detailed X-ray image of that object. Thus, the embodiment provides an in-vivo (in body) collection of X-ray images. The benefits gained from using in-vivo X-ray techniques are an increase in the detail of the image, the possibility of reducing the need for more expensive imaging procedures such as MRI and CAT scans and possibly reduce overall patient X-ray exposure.

In accordance with another embodiment, EndoFibers may be used to provide a fluorescence and/or reflectance probe. The probes are composed of "supply" light guides and "receive" light guides. In more advanced designs both of the supply and receive light guides are precisely physically arranged in complex patterns such that the optical information about the tissue being examined may be deconvoluted.

In accordance with another embodiment, dyes that may be used with fiber optic sensors are incorporated into the fiber of the EndoFiber and/or the EndoCap to provide a cost-effective and quick method for detecting various conditions. For example, a dye may be incorporated into a polymer and the polymer may be drawn into a fiber. After fabrication of these fibers, the fibers are either incorporated into the EndoFibers and EndoCaps, or used as stand alone probes.

Other features of the invention will become apparent from the following detailed description when taken in conjunction with the drawings, in which:

BRIEF DESCRIPTION OF THE DRAWINGS

FIG. 3a is a perspective view of a imaging guide endoscopic element in accordance with an embodiment of the invention;

FIG. 3b is a cross section view of the imaging guide endoscopic element of FIG. 3a;

FIG. 16 is a perspective view of a preform production processing chamber for use in forming a EndoFiber preform;

FIG. 17 is a perspective view of the preform processing chamber of FIG. 16, showing polymeric material within the chamber;

FIG. 18 is an exploded view showing removal of the rods from the preform processing chamber of FIG. 17;

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described. In addition, to the extent that orientations of the invention are described, such as "top," "bottom," "front," "rear," and the like, the orientations are to aid the reader in understanding the invention, and are not meant to be limiting.

Briefly described, the present invention provides a polymer common housing having endoscopic elements therein. Example endoscopic elements include, but are not limited to, source light channels (for illumination, hereinafter "light guides"), laser light channels (for laser ablation procedures or other laser procedures, hereinafter "laser guides"), lengthwise lumens (for therapeutic uses, insertion of instruments, irrigation, articulation, fluid transfer, biopsy channel etc.), imaging guides, and active and sensing fibers. For the purposes of this document a polymer structure that incorporates any subset of these elements is called an "EndoFiber."

By "common housing," we mean the substrate into which the endoscopic elements are mounted. The EndoFiber may be used, as examples, in the formation of an endoscopic shaft or a borescope.

As one example, an endoscope may be an instrument used for the examination of a hollow viscus such as the bladder or a cavity such as the chest. The endoscope in this example includes a camera mounted on the proximal end of an imaging guide and a light or laser source attached to a light or laser guide that transmits light to illuminate the field to be visualized via the imaging guide. In this example, the light guide and imaging guide are formed as an EndoFiber. Many other examples are given below.

Figure 1:
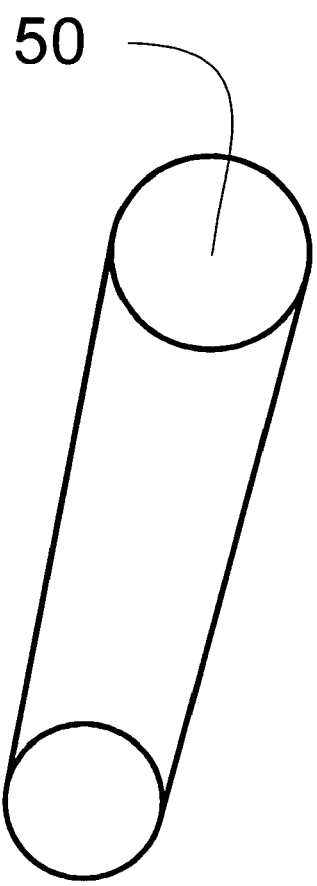
FIG. 1 is a perspective view of a laser/light endoscopic element in accordance with an embodiment of the invention.
Figure 2:
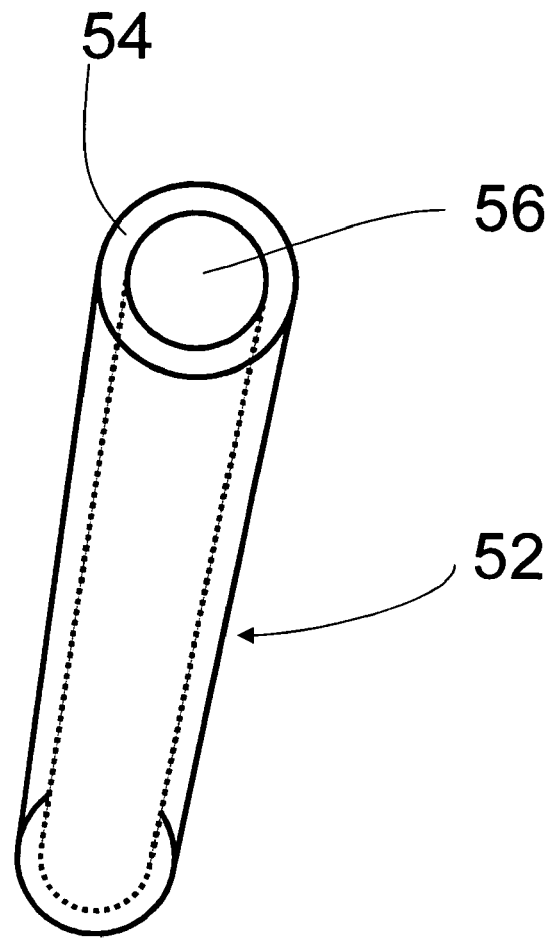
FIG. 2 is a perspective view of an alternate embodiment of a laser/light endoscopic element.

Referring now to the drawings, in which like reference numerals represent like parts throughout the several views, FIG. 1 shows one example of a light/laser guide endoscopic element 50 composed of one piece of plastic. In general, a light/laser guide is an optical fiber. FIG. 2 shows another laser/light guide endoscopic element 52 composed of two materials, an outer material 54 and an inner material 56. The outer material 54 should preferable have an index of refraction that is lower than the inner material 56 so that light will guide in the element as known in the art. Other laser/light guiding endoscopic elements may be used. For example, the element may have a graded index profile or be composed of a plurality of layers. For the sake of clarity laser/lights are generally designated 128 throughout this document.

Figures 3A, 3B:
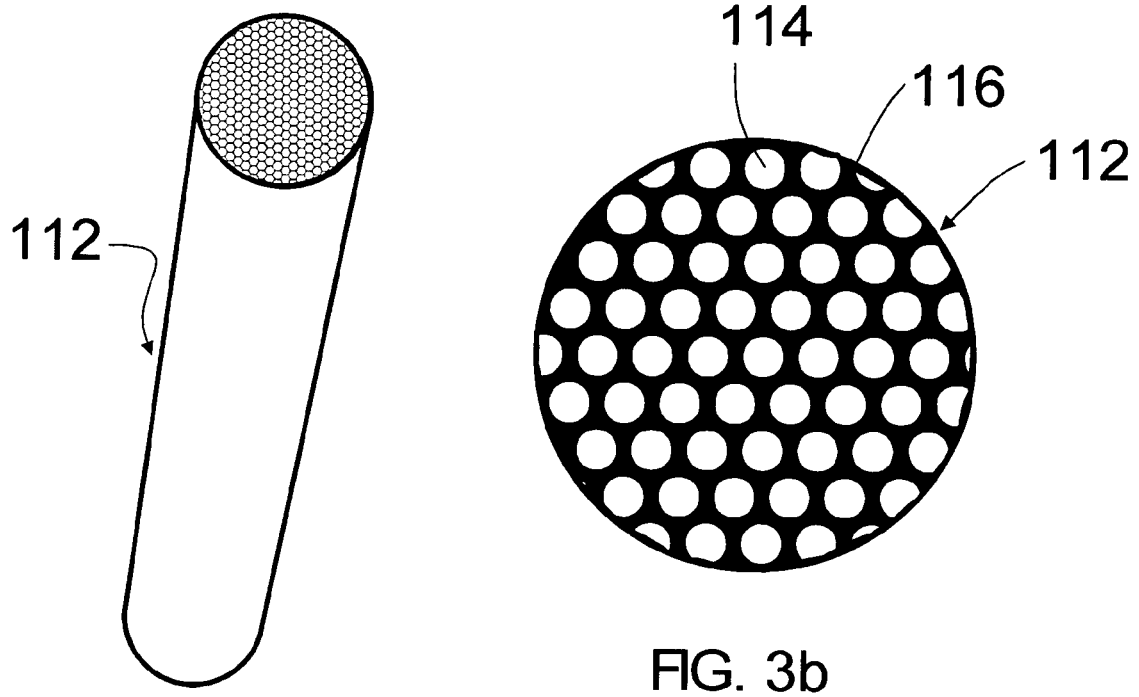

FIG. 3a shows one example of an imaging guide endoscopic element 112 composed of a plurality of optical cores 114 (FIG. 3b) encased in a common cladding 116. FIG. 3b shows a close up view of the cross section of the same imaging guide endoscopic element 112. Other imaging guide endoscopic elements may be used. For example graded index or multi-step index imaging guide endoscopic elements may be used. For the sake of clarity imaging guides are generally designated 112 throughout this document.

Figures 4, 5:
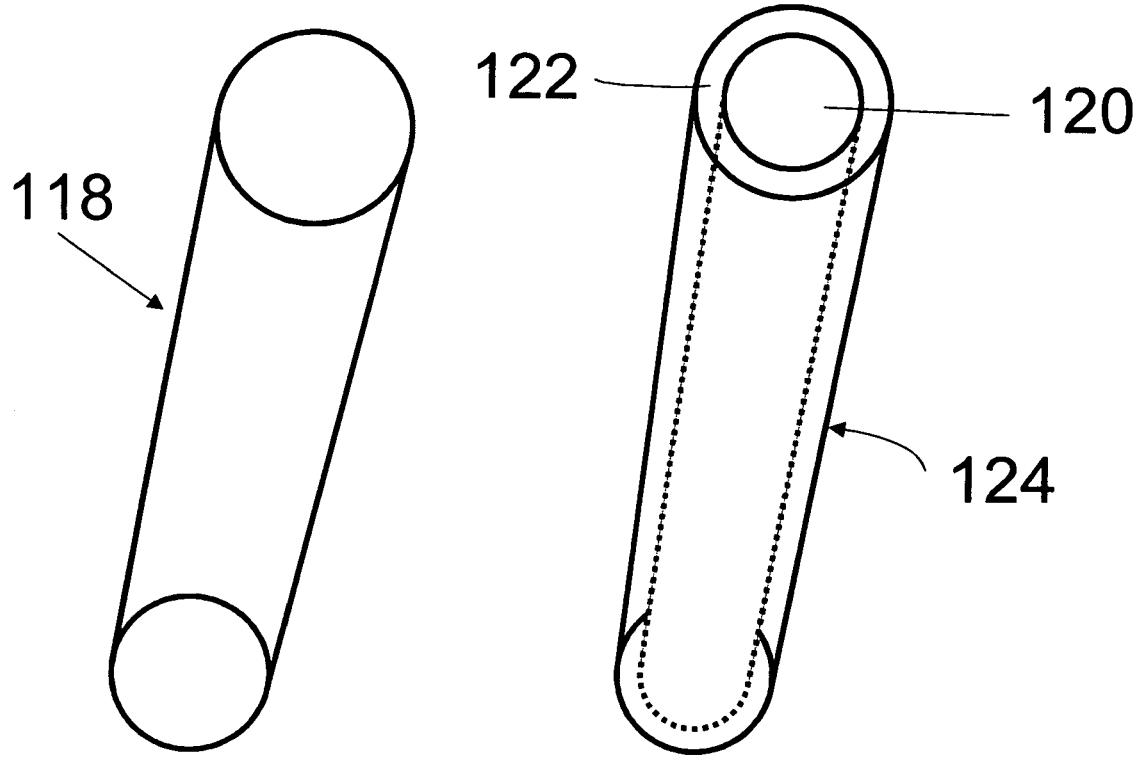
FIG. 4 is a perspective view of a lumen endoscopic element in accordance with an embodiment of the invention.
FIG. 5 is a perspective view of an alternate embodiment of a lumen endoscopic element.

FIG. 4 shows a lumen endoscopic element 118. In this example, the entire lumen endoscopic element 118 serves as a bore, and thus in use there is a complete absence of material in the position of this endoscopic element in the final EndoFiber. FIG. 5 shows another lumen endoscopic element 124, in this example the elements results in a lumen 120 surround by a material 122 (e.g., a tube) around the lumen 120 in the EndoFiber. Other lumen endoscopic elements may be used, for example multi-layered structures may be used. For the sake of clarity lumen endoscopic elements are generally designated 126 throughout this document. Each of these lumen endoscopic elements may serve as an articulation lumen, fluid transfer channel, working channel, or therapeutic access channel, as examples.

Figure 6:
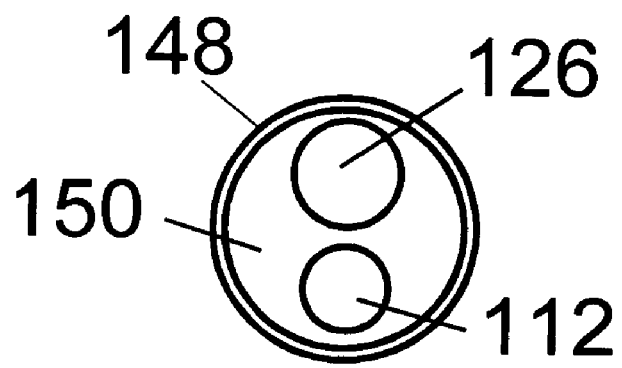
FIG. 6 is a miniaturized EndoFiber in accordance with one embodiment.

FIG. 6 shows an EndoFiber 148 in accordance with one embodiment. This EndoFiber includes a plurality (i.e. more than one) of endoscopic elements set in a common housing material 150. In the embodiment of the EndoFiber 148 shown in FIG. 6, there are the following endoscopic elements: one imaging guide 112 and one lumen 126 encased in a common housing 150. In this case the common housing 150 also serves to transmit illumination light.

Figure 7:
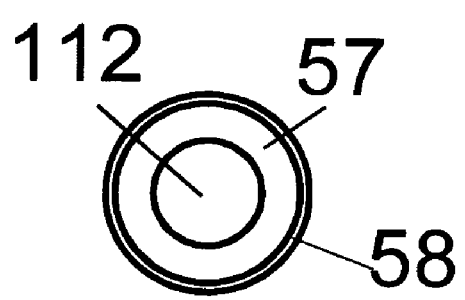
FIG. 7 is an alternate embodiment of a miniaturized EndoFiber.

FIG. 7 shows an EndoFiber 58 in accordance with one embodiment. In the embodiment shown in FIG. 7 there are the following endoscopic elements: one imaging guide 112 encased in a common housing 57. In this case the common housing 57 also serves to transmit illumination light.

Figure 8:
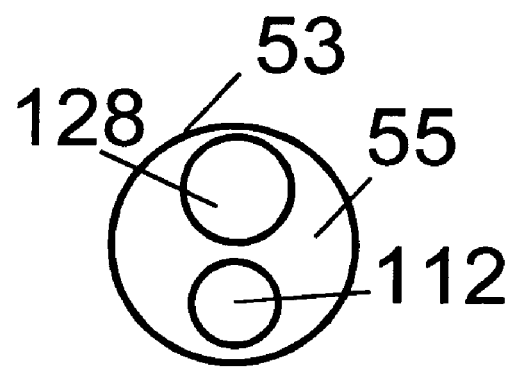
FIG. 8 is still another alternate embodiment of a miniaturized EndoFiber.

FIG. 8 shows an EndoFiber 53 in accordance with one embodiment. The EndoFiber 53 includes a plurality (i.e. more than one) of endoscopic elements set in a common housing 55. In the embodiment shown in FIG. 8 there are the following endoscopic elements: one imaging guide 112 and one light guide 128 encased in the common housing 55.

The fabrication technology described below allows for the fabrication of endoscopes with revolutionary small shaft size. For example, the EndoFibers 148 and 53 in FIGS. 6 and 8 may be produced with diameters less than 250 microns in diameter, while still providing articulation and lighting functions. Such small diameter endoscopes allow direct visualization of small structures such as anatomic features in the body that have been previously difficult or impossible to view.

Figure 9:
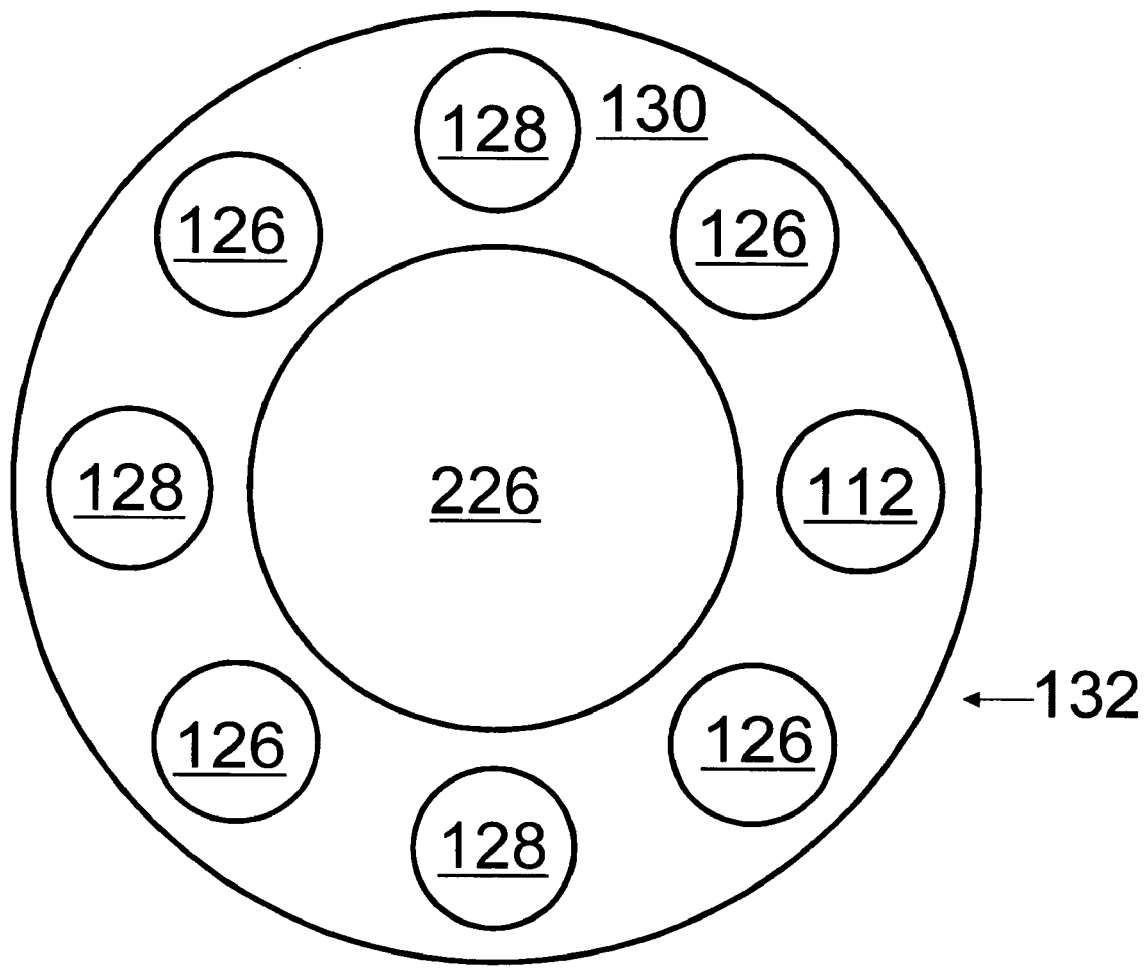
FIG. 9 is a cross-sectional view of an EndoFiber in accordance with one embodiment.
Figures 10A, 10B, 10C:
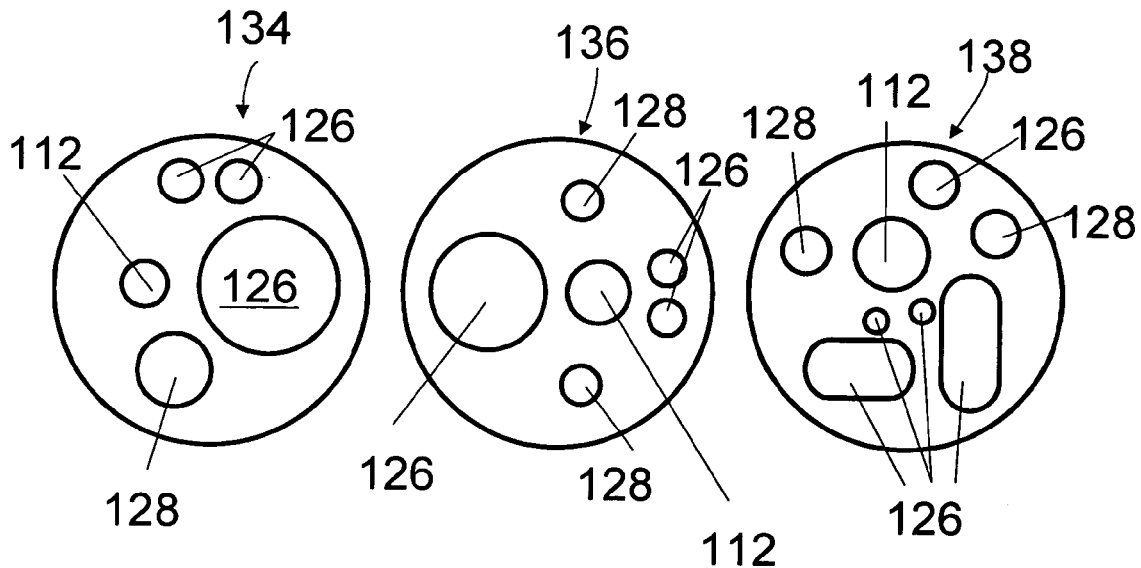
FIG. 10a-e are cross-sectional views of five different embodiments of EndoFiber profiles.
Figures 10D, 10E:
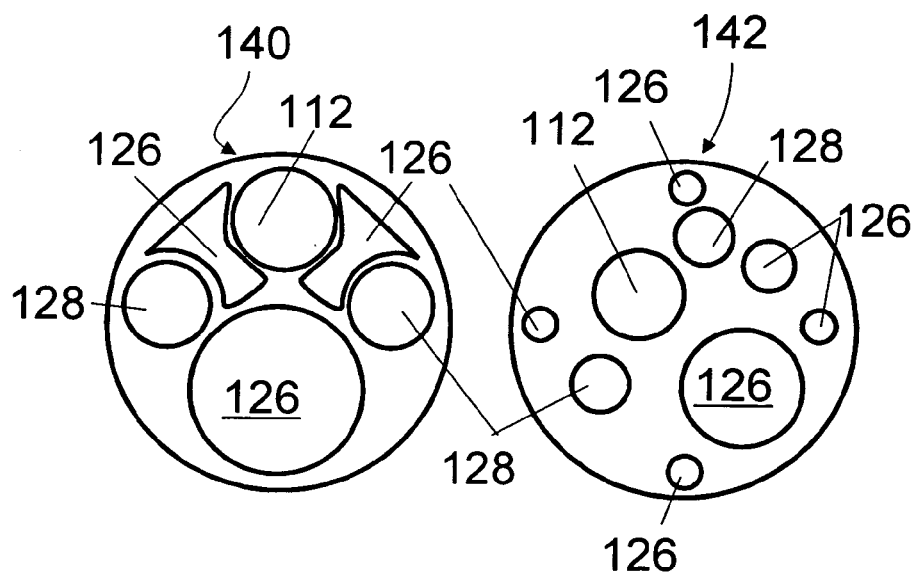

FIG. 9 shows an EndoFiber 132 in accordance with one embodiment. The EndoFiber 132 includes a plurality (i.e. more than one) of endoscopic elements set in a common housing material. In the embodiment shown in FIG. 9 there are the following endoscopic elements: one imaging guide 112, three light guides 128, four articulation lumens 126, and one working channel (lumen) 226 in the center, all encased in a common housing 130.

Although a number of different EndoFibers having different endoscopic elements have been described with reference to FIGS. 6-9, the number, type, geometrical shape, and configuration of endoscopic elements in an EndoFiber of the present invention are variable. For example, any of the endoscopic elements (lumens, light guides, imaging guides, or other elements) may be any geometrical, non-geometrical, or asymmetric shape. In addition, the geometrical shape of the common housing material is variable. For example, although the embodiments shown have circular cross sections, an EndoFiber may be any geometrical, non-geometrical, or asymmetric cross section. A person of ordinary skill in the art may use the invention described herein to create any number of different types of EndoFibers.

FIGS. 10a-10e show five examples of cross-sections of EndoFibers 134, 136, 138, 140, and 142 that are similar to endoscopic shafts in use today. The EndoFiber 134 is similar to an SIGMOIDOSCOPE endoscopic shaft produced by Pentax Corporation, the EndoFiber 136 is similar to an endoscopic PENTAX W SERIES endoscopic shaft, the EndoFiber 138 is similar to an endoscopic shaft produced by Olympus, the EndoFiber 140 is similar to an endoscopic shaft produced by Karl Storz, and the EndoFiber 142 is similar to an endoscopic shaft produced by Fuji Photo Optical. The EndoFibers 134, 136, 138, 140, 142 each include lumens 126, imaging guides 112, and laser/light guides 128.

Figure 11:
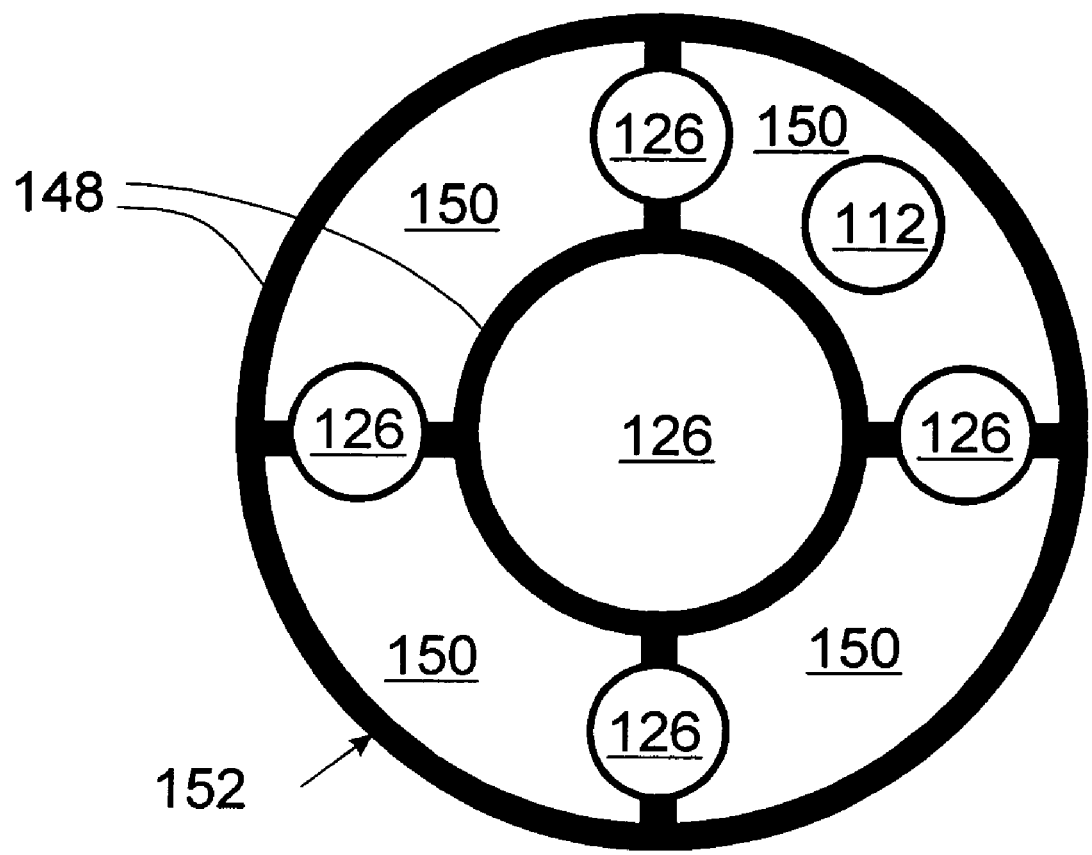
FIG. 11 is a cross-sectional view of an EndoFiber in accordance with one embodiment, the EndoFiber containing light guides that are integral with a common housing material.

In accordance with one embodiment, the common housing may also serve as a light guide. FIG. 11 shows an EndoFiber 152 in accordance with such an embodiment. In this embodiment, the common housing 150 is separated into four quadrants by an additional material 148 (also part of the common housing). Each quadrant is capable of transmitting light. The two materials 148 and 150 have different indexes of refraction such that the light will guide in the housing material 150. The refractive index of material 150 is higher than that of material 148, by preferably greater than 0.01.

Each quadrant of material 150 is optically isolated from the other quadrants, so that different colors (wavelengths) of light may be used if desired. The diameter of the EndoFiber 152 is variable, and may be formed using the methods described herein to be smaller than 0.6 mm or larger than 2 cm or in between.

The EndoFiber 152 may be used in a four-way articulating endoscope. To this end, four articulation lumens 126 are spaced about the EndoFiber 126. A central working/therapeutic channel (lumen) 126 is also provided.

The geometry of the common housing material is variable. For example, although the embodiment shown has a circular cross section, it may be any geometrical, non-geometrical, or asymmetric shape. In addition not all of the common cladding material must act as a light guide. For example only one or two of the quadrants 150 may act as light guides, each of the quadrants 150 of the housing material may act as light guides, or an entire common housing may act as a single light guide without being separated out into quadrants. A person or ordinary skill in the art may use the invention described herein to create any number of different shapes, cross-sections, or configurations of elements for the common housing in the EndoFiber.

Figure 12:
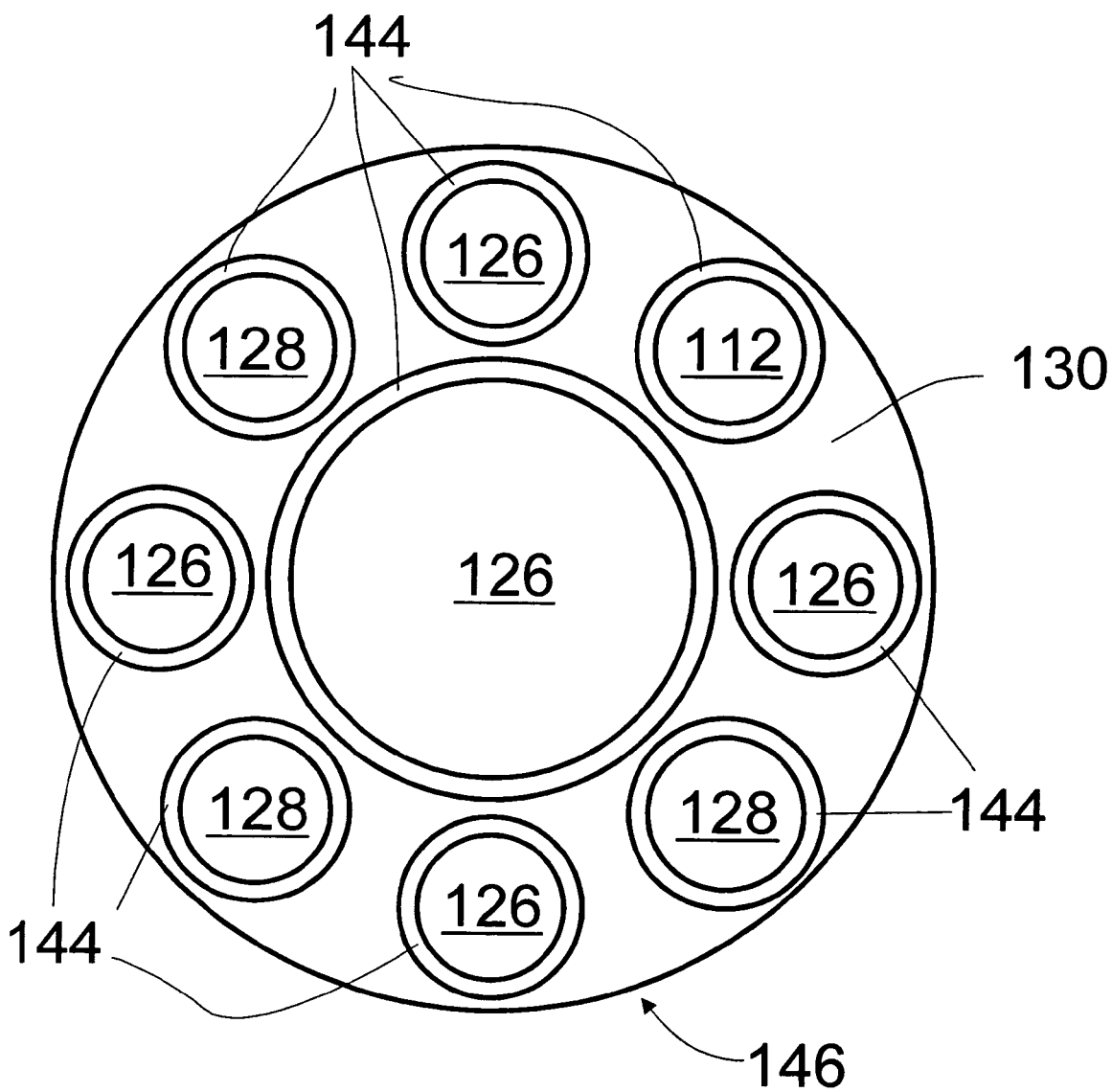
FIG. 12 is a cross-sectional view of an EndoFiber containing a protective layer in accordance with one embodiment.

In the embodiment shown in FIG. 12 there are the following endoscopic elements: one imaging guide 112, three light guides 128, four articulation lumens 126, and one central working/therapeutic channel (lumen) 126. This embodiment differs from that of FIG. 9 by the addition of a protective layer 144, or cladding material, around the endoscopic elements. In this embodiment the protective layer 144 serves to facilitate the separation of the endoscopic elements from the common housing 130. Separating the endoscopic elements may facilitate/ease construction of the final endoscopic shaft as discussed later.

The thickness of the protective layer 144 is variable. In addition, the protective layer 144 may not need to be applied around all of the endoscopic elements, as described further below.

The protective layer 144 that is used in the construction of the imaging guide endoscopic element preform may also be left on the final EndoFiber product. This process is described further below. By leaving the protective layer 144 on the endoscopic elements, the protective layer 144 serves as a protective cladding for the corresponding imaging guide endoscopic element in the final EndoFiber product. Likewise, if a light guide endoscopic element is provided with a protective layer 144, the protective layer 144 may be maintained in the final EndoFiber product to serve as a protective cladding.

In some instances it may be desirous that a section of the EndoFiber (nearest the distal end) exhibit higher flexibility than the rest of the EndoFiber. This would be beneficial for flexible endoscopes, since it is generally preferable to have a large degree of tip control for steering the endoscope while entering the various passageways of the body or to have the capability of turning the tip of the endoscope to observe a particular object. There are many ways to accomplish the objective of having greater flexibility in a section of the EndoFiber. Below are a few examples that may be combined together if desired.

For example, one method is to provide a sheath over the outside of the EndoFiber (after fabrication) that does not extend to the end of the EndoFiber. Such sheath material may be any material that has the net result of decreasing flexibility when applied to EndoFiber. Example materials include thin metals and stiff plastics. The result is that the sheath stiffens portions of the EndoFiber over which it extends, but permits other portions of the EndoFiber to be more flexible.

Figure 13:
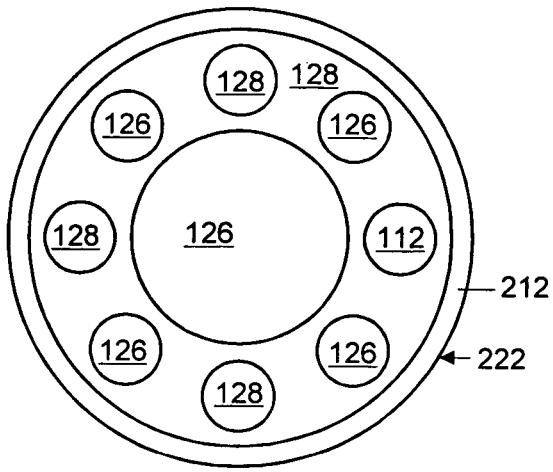
FIG. 13 is a cross-sectional view of an EndoFiber with an external stiffening member in accordance with an embodiment of the invention.

For example, another method is the EndoFiber 222 shown in FIG. 13 includes an additional outer layer 212 composed of preferably a stiffer plastic. After the outer layer 212 is drawn over the EndoFiber 222, a portion of the outer layer 212 may be removed from the end section of the EndoFiber to create a region of greater flexibility. The stiffer outer layer may be removed by a variety of means including peeling or dissolving.

For example, another method is to fabricate the EndoFiber with additional lengthwise lumens into which may be inserted stiffness members. The stiffness members do not extend to the whole length of the EndoFiber (leaving a section near the end that does not contain the stiffness members).

Figure 14:
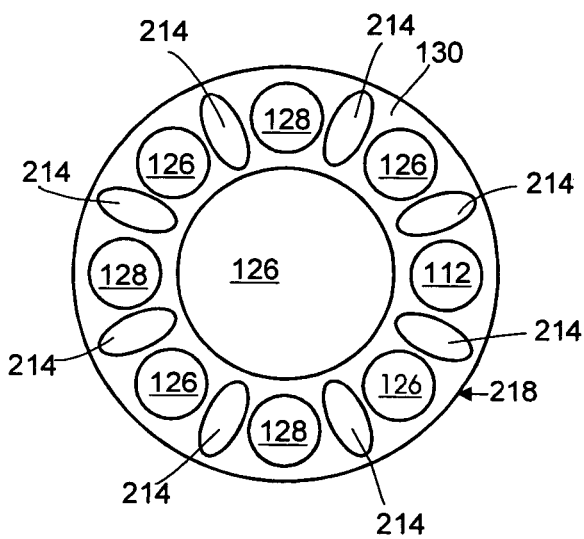
FIG. 14 is a cross-sectional view of an EndoFiber with an internal stiffening members in accordance with an embodiment of the invention.

For example, another method is the EndoFiber 218 shown in FIG. 14 includes a stiffening member 214 that has preferably a greater stiffness than the other materials in the EndoFiber (although a less stiff material will also work). After the EndoFiber 218 is formed, a section of the stiffening member 214 may be removed from the end of the EndoFiber, creating a region of greater flexibility. One method of removing this material is by dissolving the material from the end of the EndoFiber.

It is known in the art that through capillary action one material may be dissolved inside of another material that is not dissolved. The length of the dissolved region is controllable. One method of control is through the amount of time that the solvent is allowed to be present.

A variant on this method is the stiffening member 214 may be a material that does not exhibit a high degree of bonding with the material immediately adjacent to it. In this case the stiffening member 214 may be removed from a section of EndoFiber near the end by sliding/pulling/pushing the material through a section of the EndoFiber and cutting or otherwise removing it.

Additionally the stiffening member 214 may be placed into lumens in the drawn EndoFiber and then hardened. In this example, the stiffening member may be, for example, an epoxy or polymer.

Figure 15:
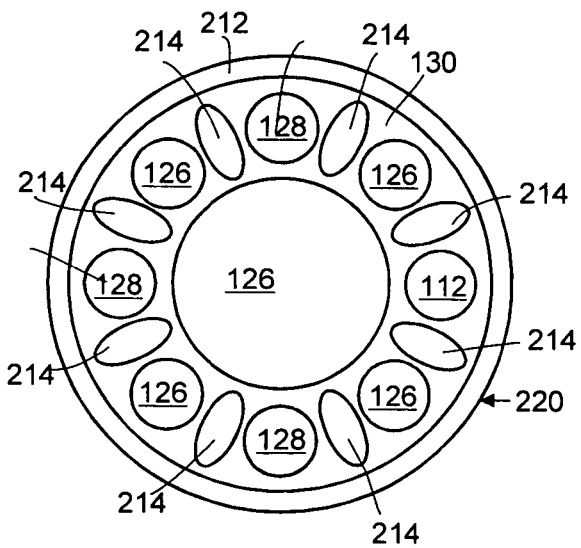
FIG. 15 is a cross-sectional view of an EndoFiber with an external and internal stiffening members in accordance with an embodiment of the invention.

These methods of stiffening a select portion of the EndoFiber may be combined together if desired. An example is shown in FIG. 15, which contains both internal 214 and external stiffening members 212, which may be subsequently removed from the end section of the EndoFiber.

In accordance with one embodiment, all of the materials out of which the EndoFibers are constructed are polymer materials, such as thermal plastics. A number of different materials may be used, but preferably the cores of the light guides 128 and the imaging guides 112 are made out of optically clear materials to facilitate the transmission of photons. In addition it is also preferred that the refractive index of the materials used for the core of the light guides and the cores of the individual pixels of the imaging guides be higher then the material immediately adjacent to it so that optical transmission may occur through the core materials in a manner known in the in the art. Example materials include cyclic olefin copolymers, polysulfone, Poly(methyl methacrylate) (PMMA), Polystyrene (PS), Zeonex, Zeonor, as well as fluoropolymers.

The common housing material may be made from an even wider selection of polymeric materials, (just about any polymer material) since in many cases it is not required to be optically clear. In some cases it is desired to have the housing material to be flexible, so as to fabricate flexible endoscopes. In this case a flexible polymer may be chosen. Example materials include Dyneon's THV materials such as THV 200, THV 500, THV 2030, polyurethanes or any other flexible polymer. If it is desired that the housing material also act as a light guide, then optically clear materials are desired for the portion the housing that will be transmitting light. Examples include the previously mentioned polymers.

All of these materials may also be doped with various dopants/compounds to enhance the EndoFiber. Example enhancements include increasing the x-ray signature or imparting additional functionality such as scintillating abilities and/or detecting/sensing abilities.

In accordance with another embodiment, the materials out of which the EndoFibers are constructed include other materials. This other materials are quite varied. They may be metal, glass, non-thermal plastics, etc. These materials are incorporated into the EndoFiber by a modified draw process (which is described later). It may be beneficial in some cases to use glass/silica light/laser and/or glass/silica imaging guides if it is desired to have light/laser guides and/or imaging guides that may transmit light (for example a higher power or different wavelength of light) with better/different characteristic than polymer materials.

Additionally other materials may be drawn into the EndoFiber. For example conductive wires may be drawn into the EndoFiber to provide electrical power to some device on the end (such as an ultrasonic transducer or other device). Another material, for example a metal, may be drawn into the EndoFiber that will be used to impart articulation to the EndoFiber. Polymer or glass photonic crystal fiber may also be incorporated into the EndoFiber in this manner.

There are a number of different methods that may be used to manufacture the EndoFiber. In accordance with one method of the present invention, as further described below, the EndoFiber may be formed by a draw process utilizing a preform. The preform may be constructed in many ways. In general, however, the EndoFiber preform may include one or more light/laser guide preforms, and/or one or more lumen preforms, and/or one or more imaging guide preforms. These structures are assembled and melded together to form the EndoFiber preform.

In accordance with one embodiment, preforms for the EndoFiber may be formed in a preform production chamber, such as a preform production chamber 60 shown in FIG. 16. The preform production chamber 60 shown in the drawings includes a hollow cylinder 62 between a top plate 64 and a bottom plate 66. Each of these members preferably includes internal surfaces that easily release from a polymeric material. For example, the top plate 64 and the bottom plate 66 may be formed of Teflon. The hollow cylinder 62 may be formed of glass, steel, Teflon, or any other suitable material. However, by forming it of glass, the interior of the preform production chamber 60 may be seen. In one embodiment, a series of rods 68 extend from the top plate 64 to the bottom plate 66 and inside the hollow cylinder 62. The rods 68 may, for example, fit into indentations in the bottom plate 66 and the top plate 64. Alternatively, the rods 68 may be attached to the top plate 64 or may otherwise be suitably arranged in the hollow cylinder 62.

Support rods 70 extend from the corners of the top plate 64 to the corners of the bottom plate 66. A vacuum attachment or hose 72 is provided on the top plate 64, and is in fluid communication with the interior of the preform production chamber 60.

In use, the preform production chamber 60 may be prepared with a mold release agent such as is known in the art. The mold release agent is applied to the inner surfaces of the preform production chamber 60 and to the rods.

After the mold release agent is applied, the preform production chamber 60 is filled with the polymeric material that is used to form the common housing preform for the EndoFiber preform. The polymeric material may be applied in at least two different states: as a plastic monomer liquid, which is subsequently polymerized by one of the many methods known in the prior art, or as solid plastic pellets, tubes, rods, fiber or other small form pieces of plastic that are solid, combination gel or slurry combining both may be used. The different methods for handling the liquid and solid polymeric materials are addressed in the following paragraphs.

If solid plastic pellets or other small solid pieces are used, then the solid material is melted in the preform production chamber 60 under vacuum (similar vacuum pressures to those discussed above may be used). The solid plastic may be washed prior to use, for example with distilled water. If washed, the solid plastic is preferably washed in a dust-free environment, (class 10,000 or better), and is baked above 100 degrees Celsius for at least 4 hours to remove all water.

When melting, the plasticized material forms around the rods 68 and inside the hollow cylinder 62. The polymeric material, which eventually becomes the common housing preform for the EndoFiber preform, is shown in the preform production chamber 60 in FIG. 17 generally by the reference numeral 80.

Regardless of the state of the polymer material used, after the polymeric material has been polymerized or melted into the form of the interior of the preform production chamber 60, the top plate 64 is removed, such as is shown in FIG. 18. The rods 68 for endoscopic elements other than lumens are then pulled out of the common housing material preform 80. To this end, the rods 68 include a nonstick surface, such as Teflon or mold release, which permits removal of the rods 68 from the polymerized housing preform 80. Removal of the rods 68 leaves a series of elongate holes or voids 82 through the common housing material preform 80.

The common housing material preform may also be formed by injection molding or by extrusion. Both of these processes are well known in the art.

Figure 19:
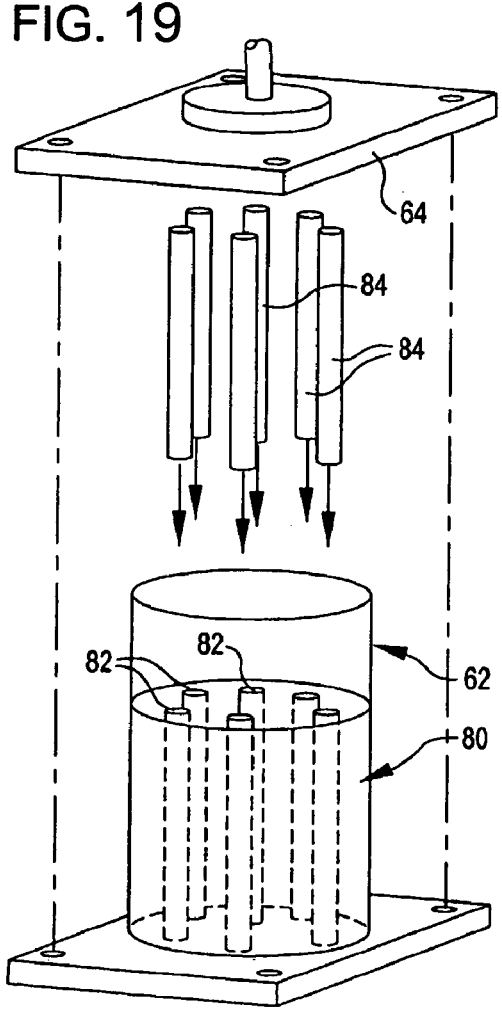
FIG. 19 is an exploded perspective view showing insertion of Endoscopic element preforms into the preform production processing chamber of FIG. 16.

As can be seen in FIG. 19, endoscopic element preforms 84, such as the light guide, imaging guide, and lumen preforms, are then inserted into the holes or voids 82 in the housing preform 80. The lumen endoscopic elements may be formed in at least three methods. First, the rods 68 may be left in EndoFiber preform at this point and their later removal provides lumens. Second, the original rods 68 may be removed and replaced with smaller rods that have a layer of a different polymer around them (to form the lumens 52 of FIG. 2). Third, a material may be inserted in the hole to be removed later in the process, such as through dissolving. Preferably, the endoscopic element preforms 84 fit snugly into the voids or holes 82, so that no voids or air gaps are formed in the final EndoFiber preform 90.

Figure 20:
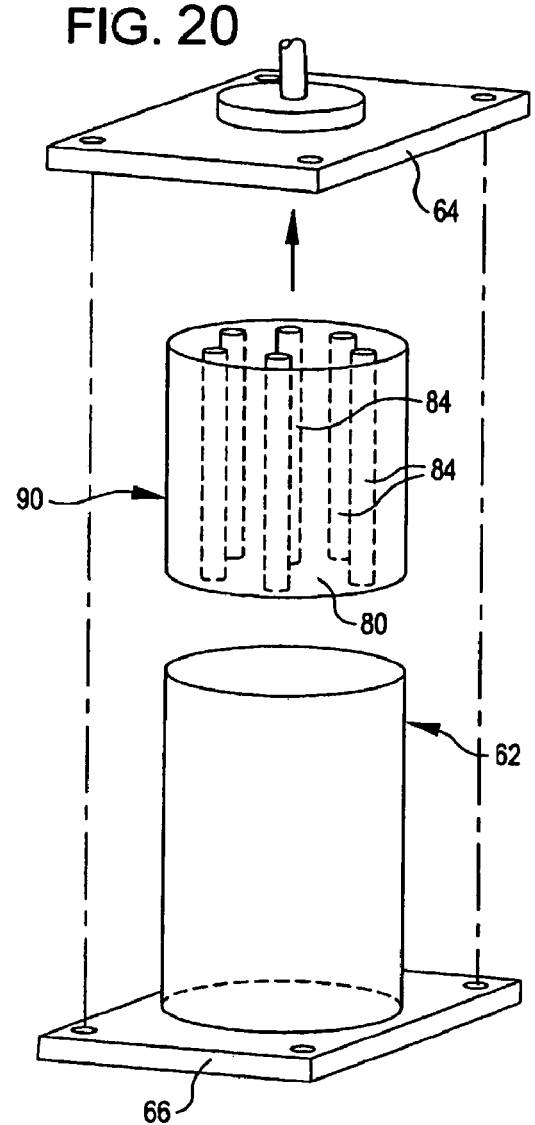
FIG. 20 is an exploded perspective view showing removal of an EndoFiber preform from the preform processing chamber of FIG. 16.

The top plate 64 is then replaced, if desired vacuum is applied or this may also be carried out without vacuum being applied, and the combined endoscopic element preforms 84 and the common housing preform 80 are heated. In this manner, the endoscopic element preforms 84 and the housing preform 80 meld together. After polymerization, the combined housing preform and endoscopic element preforms are removed from the hollow cylinder 62, as shown in FIG. 20. The remaining rods for the lumen endoscopic elements are then removed or dissolved away. Alternatively, they may be left in and dissolved away after drawing the EndoFiber. The removed, combined, housing preform 80 and endoscopic element preforms 84 form the EndoFiber preform 90.

In accordance with another embodiment, preforms for the housing material of the EndoFiber 26 may be formed in a preform production chamber (e.g., the preform production chamber 60 shown in FIG. 16) around endoscopic element preforms. Endoscopic element preforms (with or without cladding) are inserted into the preform production chamber 60, which is then filled with the polymeric material that is used to form the bulk of the common housing preform for the EndoFiber preform. The polymeric material for the common housing preform may, for example, be applied as a plastic monomer liquid, slurry, gel, or solids, as described above. The common housing preform material is then polymerized around the endoscopic element preforms, and the two are polymerized together as described above so that they meld together.

It is to be understood that either type of method, or other methods, may be used to form the EndoFiber perform 90. In addition, the EndoFiber perform 90 may be machined after being formed so as to form a particular shape. Alternatively, the EndoFiber preform 90 may be used as formed in an annealing or preform production chamber process. The EndoFiber preform 90 is then ready for a draw process (described next) to form the EndoFiber.

Figure 21:
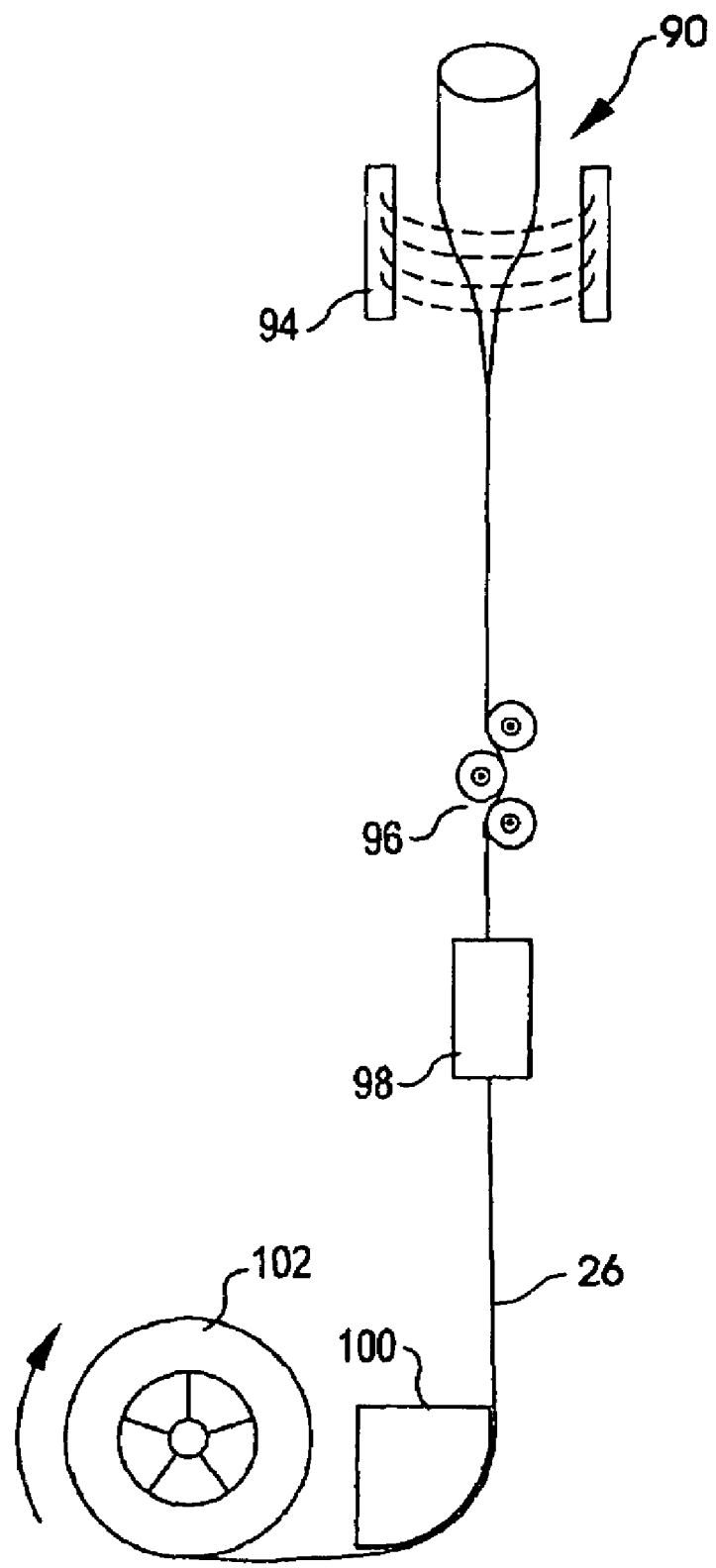
FIG. 21 is a diagrammatical view of a draw process that may be used to from an EndoFiber in accordance with an embodiment of the invention.

A draw process for creating an EndoFiber 26 is shown schematically in FIG. 21. The draw process shown there is known in the art, and differs only in that the EndoFiber preform 90 (not known in the art) is used in the draw process. Although draw processes are well known in the art, a brief description is given here for the aid of the reader.

In the draw process of FIG. 21, the EndoFiber preform 90 is located between and in a radiative heat oven 94. The heat oven 94 heats the EndoFiber preform 90 so that it is flowable, and flowable plastic from the bottom of the EndoFiber preform 90 is drawn through a tension gauge 96 and a diameter gauge 98 around a turn guide 100 and onto a take-up spool 102. The take-up spool 102 rotates at a rate that is sufficient to draw fiber (in this case, the EndoFiber 26) at a rate from the EndoFiber preform 40 so that the fiber is a substantially constant diameter. The diameter gauge 98 passively checks the diameter of the fiber that is being drawn. To allow proper drawing of the EndoFiber preform 90, the materials of the EndoFiber preform preferably must have melting temperatures that are substantially the same so that they may be drawn at a single temperature. More specifically, the melting temperatures of the core material and the cladding material should be within 150 degrees Celsius of one another. Alternately, any combination of polymers chosen for use in manufacturing the EndoFiber may have a similar electromagnetic radiation cross section for a given range of wavelengths as emitted by the heat source used in the draw process.

Figure 22:
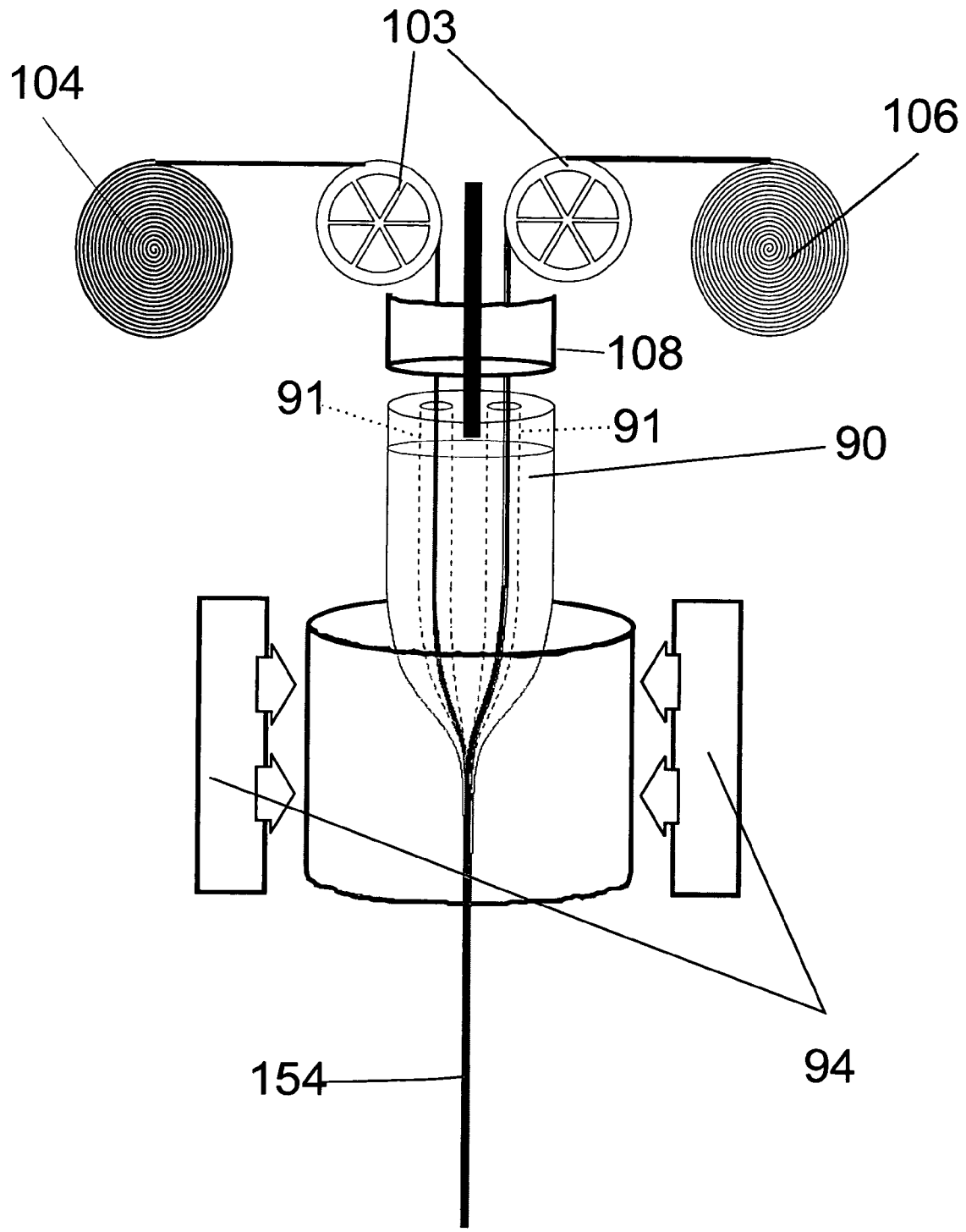
FIG. 22 is a diagrammatical view of a portion of the draw process of FIG. 21 that may be used to form an EndoFiber that contains other materials.

Alternatively a novel modified draw process may be used to incorporate non-drawable materials or other materials into the EndoFiber. The top portion of the draw tower that may be used for such a process is shown in FIG. 22. This draw process is similar to that described previously except that there are spools 104 and 106 (which hold the non-drawable material to be incorporated) located at the top of the draw tower that allow material to be pulled into holes 91 in the EndoFiber preform 90 as the same holes shrink during the draw process. Two spools are shown but any number may be used. Preferably alignment device(s) 108 and/or guide wheels 103 are used at the top to precisely control the location of the material to be incorporated into the eventually-drawn EndoFiber 154. The material to be incorporated is first fed through the proper holes 91 in the EndoFiber preform 90 and secured to either the bottom of the preform or onto the take-up wheel (not shown in FIG. 22, but similar to the take-up wheel 102 in FIG. 21). As the EndoFiber preform 90 drops during the beginning of the draw process, the holes 91 through which the material has been fed collapse inward adhering to the material and pulling it off the spools and along with the EndoFiber 154 as it is drawn.

Articulation wires may be drawn into the EndoFiber 154 in this manner. If articulation wires are drawn into the EndoFiber 154 it is preferable to either coat the wire or line the channel into which the articulation wire is to be drawn with a material that may be easily removed after drawing. Such coating materials may be a water-soluble polymer such as polyvinyl alcohol (PVA). In this manner, the articulation wire may be detached from the EndoFiber and remain in the EndoFiber by immersing the EndoFiber in water.

Wires used to conduct electricity may also be drawn into the EndoFiber in this manner. Such wires may be used to supply electrical power to devices attached later to the distal end of the EndoFiber 26, such as at the end of an endoscopic shaft.

Other materials may be added to the EndoFiber 26 using this technique. For example, a glass imaging guide, a polymer photonic crystal fiber, or a glass photonic crystal fiber may be incorporated in the EndoFiber 26 in this manner.

After the EndoFiber 154 or 26 has been formed (by any of the processes described above or by other methods), it may be connected to a connector or connectors, which connect to the rest of the endoscope, and to distal end optics. Instruments, pull wires, guide wires and other endoscope elements may also be inserted into the lumens in the EndoFiber 154 or 26 at this time.

Features of an EndoFiber in accordance with the present invention may be arranged or formed to facilitate the construction of an endoscope shaft. For example, as further described below, the endoscopic elements may be easily separable from the common housing so that optics and other devices may be attached to the endoscopic elements.

For example, for the EndoFiber 146 shown in FIG. 12, the endoscopic elements 112, 126, 128 may be separated from the common housing 130 and each other by various methods. In one method, a peeling method, the materials that form the common housing 130 and the protective layer 144 are selected such that they do not bond well with each other. To separate the endoscopic elements in this embodiment, the common housing 130 is peeled away from the endoscopic elements 21, in much the same ways as plastic electrical insulation is removed from copper electrical wires. This process leaves the endoscopic elements 112, 126, 128 protruding from the rest of the EndoFiber 146.

Figure 23:
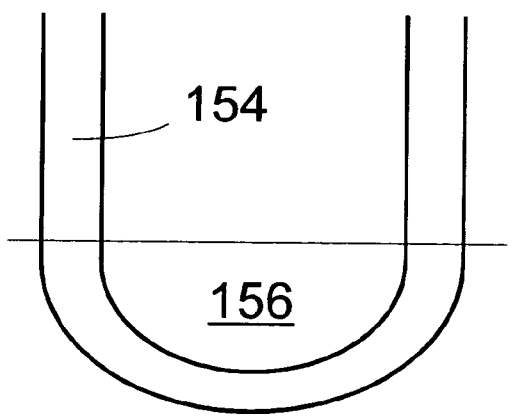
FIG. 23 is a diagrammatical view of an EndoFiber dipped into a solvent.
Figure 24:
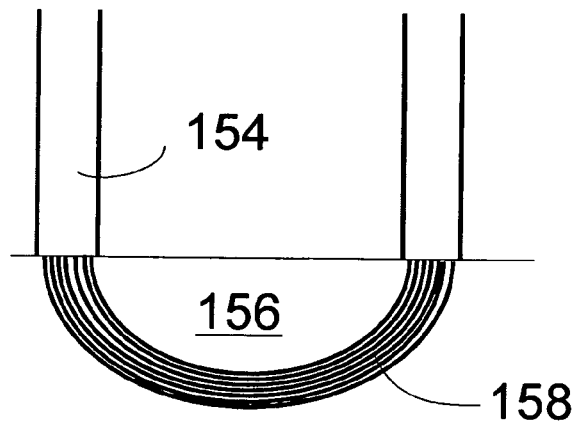
FIG. 24 is a diagrammatical view of the EndoFiber of FIG. 23 after common housing material has been dissolved leaving the endoscopic elements bare.
Figure 25:
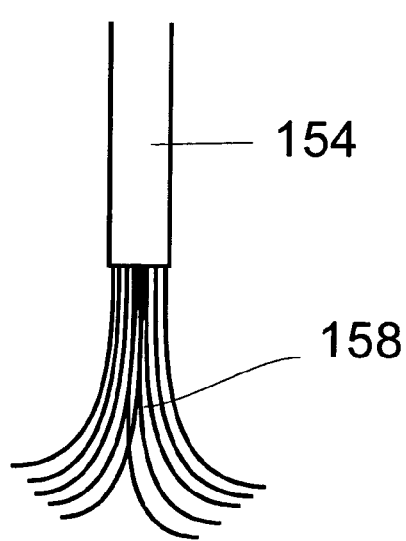
FIG. 25 is a diagrammatical view of the EndoFiber of FIG. 24 after the endoscopic elements have been cut.

In other method, a dissolving method, the materials that form the common housing 130 and the protective layer 144 are such that common housing is dissolvable by a solvent 156 (FIG. 23) that does not affect the protective layer. To separate the endoscopic elements (indicated by 158 in FIG. 24) in this embodiment the common housing is dissolved by inserting the EndoFiber 154 in solvent 156 (FIG. 23), leaving the endoscopic elements 158 (FIG. 24) protruding from the rest of the EndoFiber. The EndoFiber 154 may then be removed and the endoscopic elements 158 may be cut, leaving the EndoFiber with exposed endoscopic elements as shown in FIG. 25.

Figure 26:
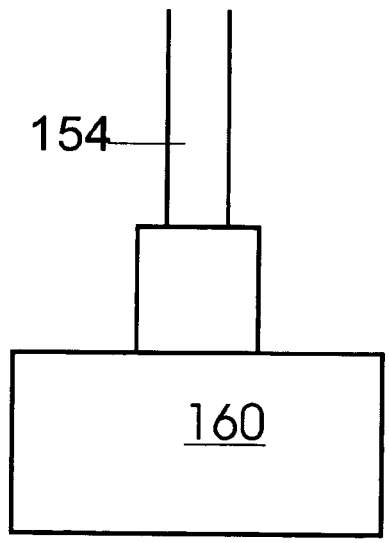
FIG. 26 is a diagrammatical view of the EndoFiber of FIG. 25 after the endoscopic elements have been inserted into a connector.

Example materials that may be used for the common housing and the endoscopic elements 158 in this embodiment include THV 200 (for the common housing) which is dissolvable by acetone and THV 500 (for the endoscopic elements, or protective layer) which is unaffected by acetone. The protruding endoscopic elements 158 may then be attached to a suitable connector 160 (this connector connects to the endoscope body or control unit) as shown in FIG. 26.

The present invention also presents methods to facilitate the construction of a completed endoscope shaft and endoscope by facilitating construction of the distal end of the endoscopic shaft. Most endoscopes have a lens at their distal end, which is typically bonded in one fashion or another to the end of the imaging guides. We have invented a mechanism that facilitates the placement of lenses and other optics on the end of an EndoFiber, called an EndoCap. The EndoCap is simply a short section of EndoFiber, having a lens and/or other optics in place of the imaging guide and/or light guides. EndoCaps may be manufactured as EndoFibers that are subsequently sliced into small sections for use, or as injection-molded parts.

Figure 29:
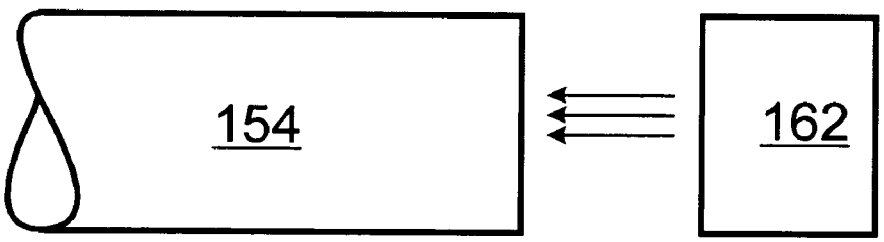
FIG. 29 is a diagrammatical view of attaching EndoCaps using a direct bonding method.

There are at least three methods for bonding EndoCaps to EndoFiber: direct bonding (FIG. 29), sheath-attaching (FIG.

Figure 27:
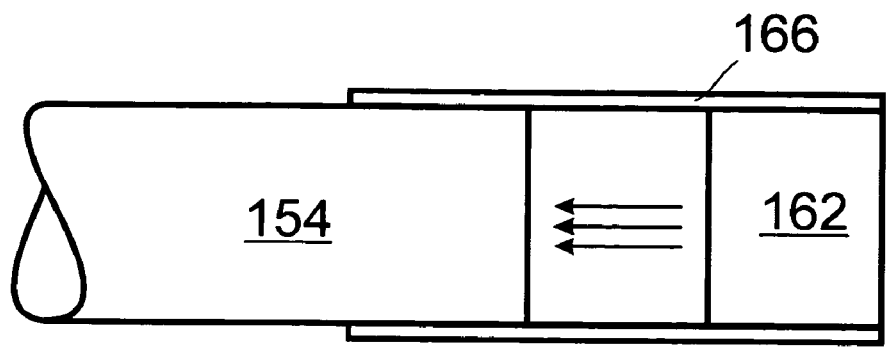
FIG. 27 is a diagrammatical view of attaching EndoCaps using a sheath attach method.
Figure 28:
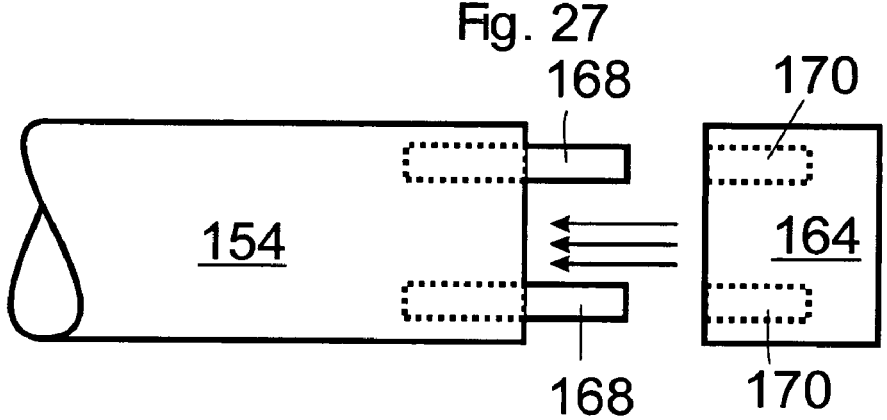
FIG. 28 is a diagrammatical view of attaching EndoCaps using a guide pin attach method.

27), and guide pin attaching (FIG. 28). An EndoCap 162 and a sheath 166 may be injection molded or attached together through a direct bonding method such as is shown diagrammatically in FIG. 27. The EndoFiber 154 is inserted into the sheath to attach the EndoFiber to the EndoCap 164.

In FIG. 28, guide pins 168 extend from the EndoFiber 154 and are attached to holes 170 on an EndoCap 164. The EndoCap 164 and guide pins 168 may be also be injected molded as one piece, which removes the requirement for guide pin holes 170. The guide pin holes in the EndoFiber may be holes left by stiffening members or may otherwise be provided.

Figure 30:
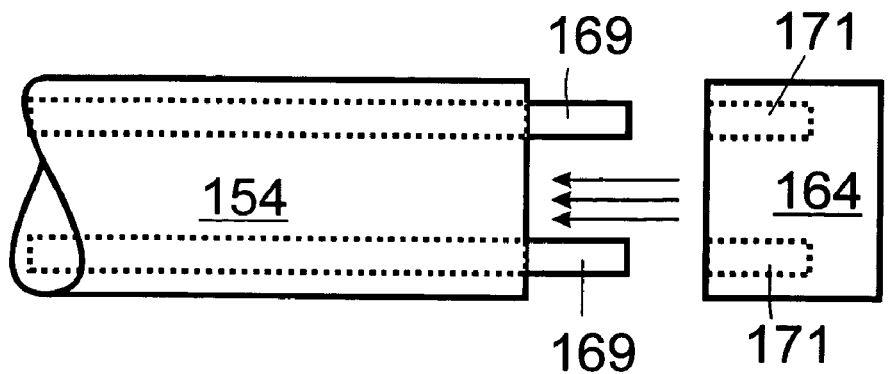
FIG. 30 is a diagrammatical view of attaching EndoCaps using an articulation wire attach method.

Alternatively, articulation wires 169 may be used to attach an EndoCap 164 to the EndoFiber 154, as shown in FIG. 30. The articulation wires 169 are attached to articulation wire holes 171 in the EndoCap 164.

An EndoCap may provide therapeutic, cost saving enhancements as well. As a section below explains, sensing chemicals, in the form of dopants, may be added to polymer image and/or light guides. Such sensing chemicals are often costly; to save costs the chemicals may be used in the small-size EndoCap as opposed to doping the entire EndoFiber. This will also increase the number of different active or sensing dopants that may be utilized thereby increasing the number of parameters or conditions that may be detected or sensed. Doping an EndoCap may also facilitate the manufacture of scintillating EndoFibers, which are described in the following section. The EndoCaps also have the added benefit that additional optics may be incorporated if the EndoCap is injection molded.

Figure 31:
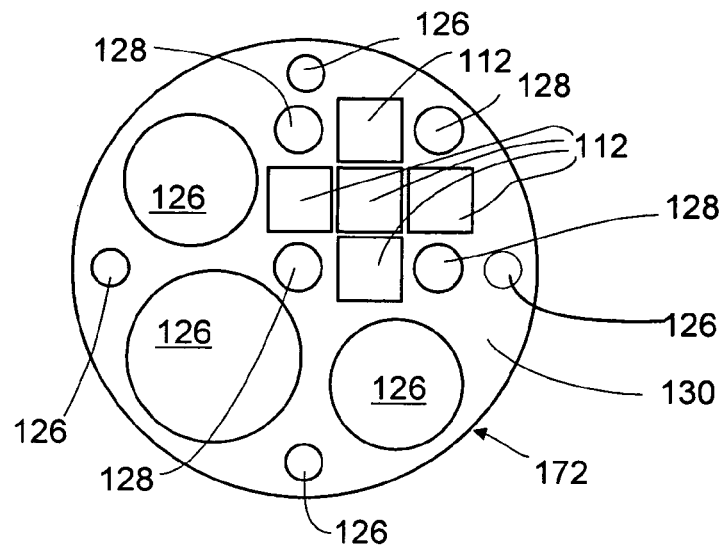
FIG. 31 is a cross-sectional view of an EndoFiber in accordance with one embodiment.
Figure 32A:
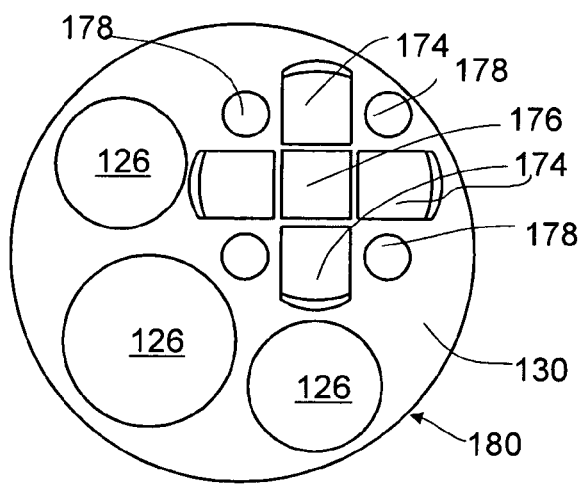
FIG. 32a is a top view of an EndoCap in accordance with one embodiment.
Figure 32B:
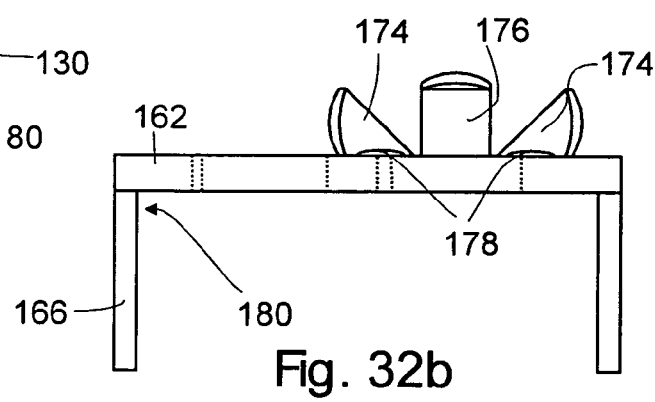
FIG. 32b is a side view of the EndoFiber of FIG. 31.

In one embodiment of the present invention, an EndoFiber 172 has a cross section as shown in FIG. 31, wherein are contained four articulation lumens 126, three therapeutic lumens 126, four light guides 128, and five square imaging guides 112. An EndoCap 180 for fitting onto the EndoFiber 172 is shown in cross section in FIG. 32a, and in side view in FIG. 32b. The EndoCap 180 contains the same elements as the EndoFiber 172 in FIG. 31 with the exception that the imaging guides and light guides are replaced by optical elements 174, 176, and 178 that manipulate the direction and/or focus/defocus the light, and the articulation lumens are not present. In this embodiment the optics 174 and 176 are designed such that the imaging guides 112 transmit images that are gathered from five different directions (the four sides and the forward/top direction). This embodiment allows the endoscope operator to view multiple directions without moving the endoscope's distal end. The operator may, as examples, view five images on five screens, all five on the same screen, or switch between views on the same screen.

As in the previous embodiments, the endoscopic elements as well as the EndoCaps composition, location, shape, size and geometry are variable. For example, the five imaging guides 112 may alternatively be provided as one cross-shaped imaging guide 112, or the optics on the EndoCap 180 may be configured to view at different angles. However, the fact that the imaging guides 112 are placed together permits the five imaging guides 112 to be injection molded in one piece. The operator can view five images on five screens, all five on the same screen, or switch between views on the same screen.

Figure 33:
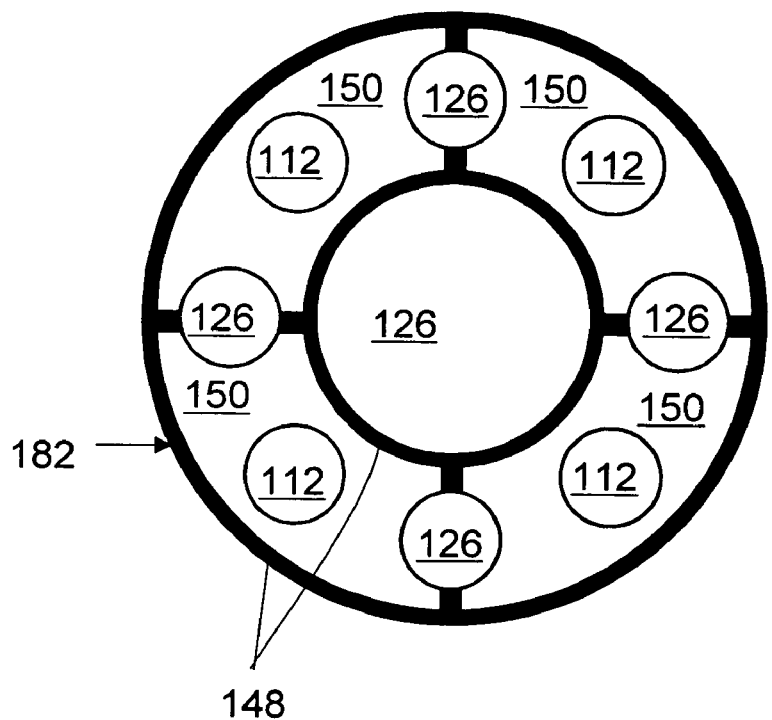
FIG. 33 is a cross-sectional view of an EndoFiber in accordance with one embodiment.
Figure 34:
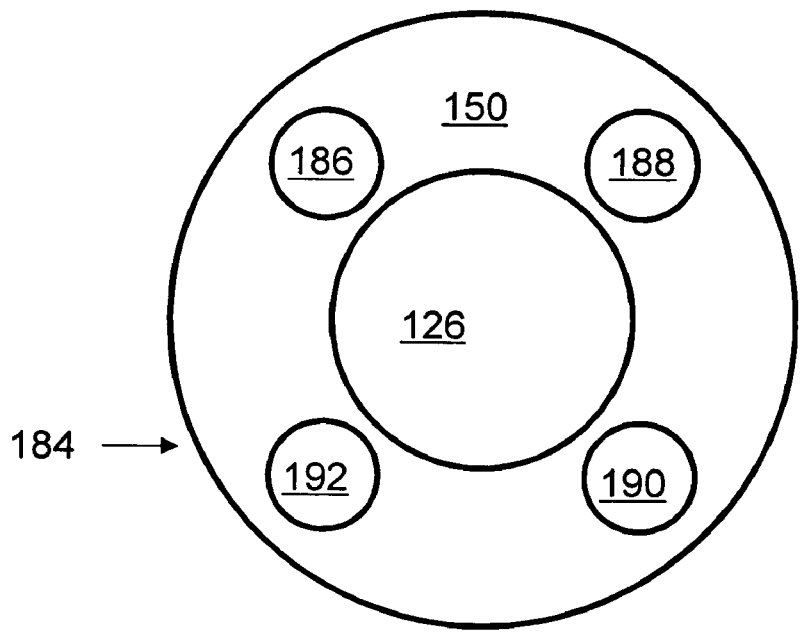
FIG. 34 is a top view of an EndoCap in accordance with one embodiment.

In another embodiment of the present invention an EndoFiber 182 has a cross section as shown in FIG. 33, wherein are contained four articulation lumens 126, one central therapeutic lumen 126, four light guides 150 (in this case integral with the common housing), and four imaging guides 112. An EndoCap 184 for fitting onto the EndoFiber 182 is shown in cross section in FIG. 34. The EndoCap 184 contains the same elements as the EndoFiber 182 in FIG. 33 with the exception that the imaging guides and light guides are replaced by optical elements 186, 188, 190, and 192 that manipulate the direction and/or focus/defocus the light and the articulation lumens are omitted. In this embodiment the optical elements 186, 188, 190, and 192 are designed such that each individual imaging guide 112 transmits images that are gathered from the same spot but with differing degrees of magnification. Standard glass lens or inexpensive plastic injected molded lens may be used, as examples.

The EndoFiber 182 and the EndoCap 184 allow an endoscope operator to view the same location with different degrees of magnification or detail. Using a different lens design 186, 188, 190, and 192 on the distal end for each imaging guide 112 allows each imaging guide 112 to carry an image of an object viewed through the imaging guides with different magnification levels. Through proper lens design and placement (known in the art), each imaging guide may have the same focal point. This would be equivalent to having a microscope endoscope with four magnification levels. This would allow for the locating of an object macroscopically followed by inspection microscopically with one instrument. As in the previous embodiments the endoscopic elements in the EndoFiber as well as the EndoCaps elements: number, composition, location, shape, size, etc. are variable.

Figure 35:
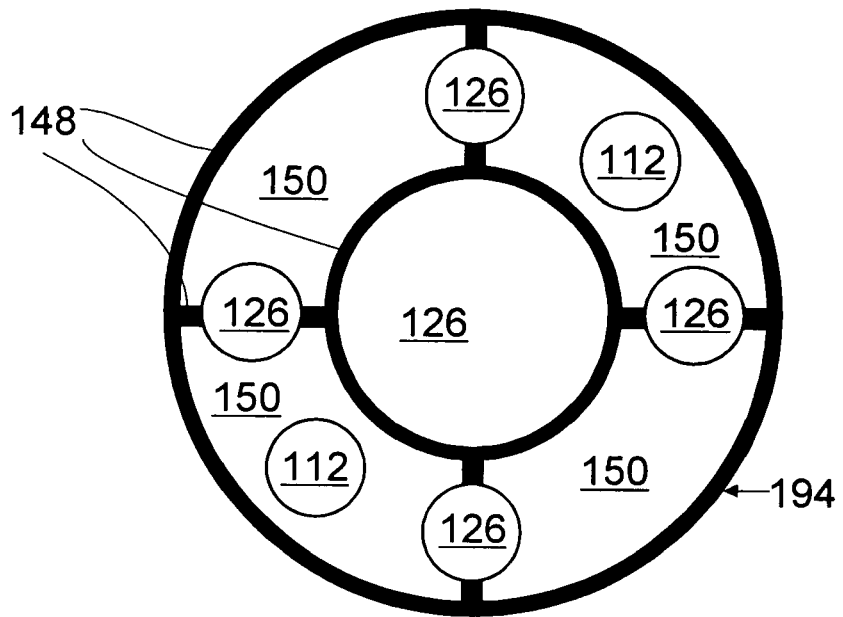
FIG. 35 is a cross-sectional view of an EndoFiber in accordance with one embodiment.
Figure 36:
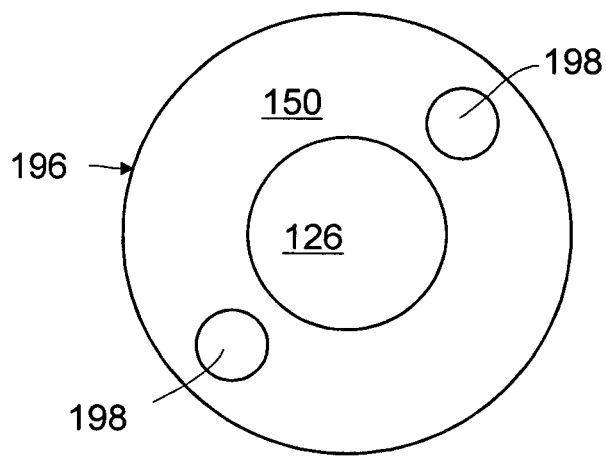
FIG. 36 is a top view of an EndoCap in accordance with one embodiment.

In another embodiment of the present invention an EndoFiber 194 has a cross section as shown in FIG. 35, wherein are contained four articulation lumens 126, one therapeutic lumen 126, four light guides 150 (in this case integral with the common housing), and two imaging guides 112. Different EndoCaps may be used on this EndoFiber. One EndoCap 196 is shown in FIG. 36, which contains the same elements as the EndoFiber 194 in FIG. 35, with the exception that the imaging guides and light guides are replaced by optical elements 198 that manipulate the direction and/or focus/defocus the light, and the articulation lumens are omitted.

The EndoFiber 194 has two imaging guides 112, allowing for three-dimensional visualization. That is, if the optical elements 198 are arranged to direct the focal points of the two imaging guides to the same location, three-dimensional viewing of the location is provided. To provide a surgeon with this enhanced effect, the surgeon could be equipped with a headset that includes small LCD screens for each eye, for example.

Figure 37:
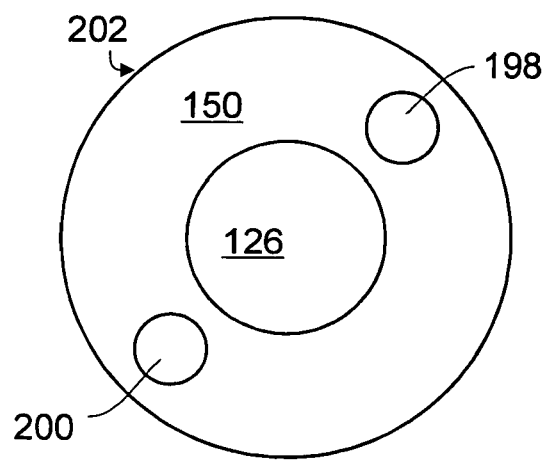
FIG. 37 is a top view of an EndoCap in accordance with one embodiment.

Another EndoCap 202 that may be used with this EndoFiber 194 is shown in FIG. 37, which contains the same elements as the EndoFiber in FIG. 35 with the exception that the imaging guides and light guides are replaced by optical elements 198 that manipulate the direction and/or focus/defocus the light. In this embodiment one of the imaging guides is replaced by a scintillating imaging guide 200 (an imaging guide that contains within it cores doped with a scintillating material). An endoscope that contains a scintillating imaging guide may be used to obtain a highly detailed X-ray image of an object from inside of another object (the body), as described in the following paragraphs.

Scintillating fibers (an example of active fiber) convert electromagnetic radiation from one portion of the spectrum to another, such as converting X-rays to visible light. Scintillating material is used in dental and medical X-ray systems. Currently a scintillating material is coated onto the end of a taper or a faceplate. The problem with using a coating is that the generated visible light may undergo several scattering events before reaching the taper or faceplate, thereby blurring the image. Scintillating material is difficult and expensive to incorporate into glass as known in the prior art, however such materials may be easily and directly incorporated into polymer. One of the driving factors behind this use of scintillating materials is that it eliminates the costly and environmentally hazardous (silver content) X-ray film and fixers.

Not only will scintillating fibers have direct applications for the current dental and medical X-ray systems, but they will also enable new applications. For instance, an endoscope that contains both an imaging guide and a scintillating imaging guide may be fabricated such that a doctor could visually locate an object and then use X-rays or other light to obtain a detailed X-ray image of that object. To our knowledge, this would be the first in-vivo (in body) collection of X-ray images. The benefits gained from using in-vivo X-ray techniques are an increase in the detail of the image, the possibility of reducing the need for more expensive imaging procedures such as MRI and CAT scans and possible reducing overall patient X-ray dosage. This could also allow for new procedures such as measuring plaque buildup on artery walls.

Plastic scintillators themselves are known in the prior art. Quite often the scintillating dopant material is a phosphor, the most common of which is Gadolinium (Gd) oxysulfide. This material along with several others may be used; examples include Gadolinium, as well as rare earths in chelate complexes such as FOD and TMHD. These compounds perform well; as the ligands act to physically separate the rare earth elements from each other (which helps in the reduction of concentration quenching) when using FOD and TMHD complexes (and other polymer additives) with Rare Earths (Er, Yt, Nd). The scintillating imaging guides are then used to manufacture scintillating faceplates and tapers. Scintillating imaging guides are incorporated into EndoFiber caps in the same manner as standard imaging guides.

Figure 38:
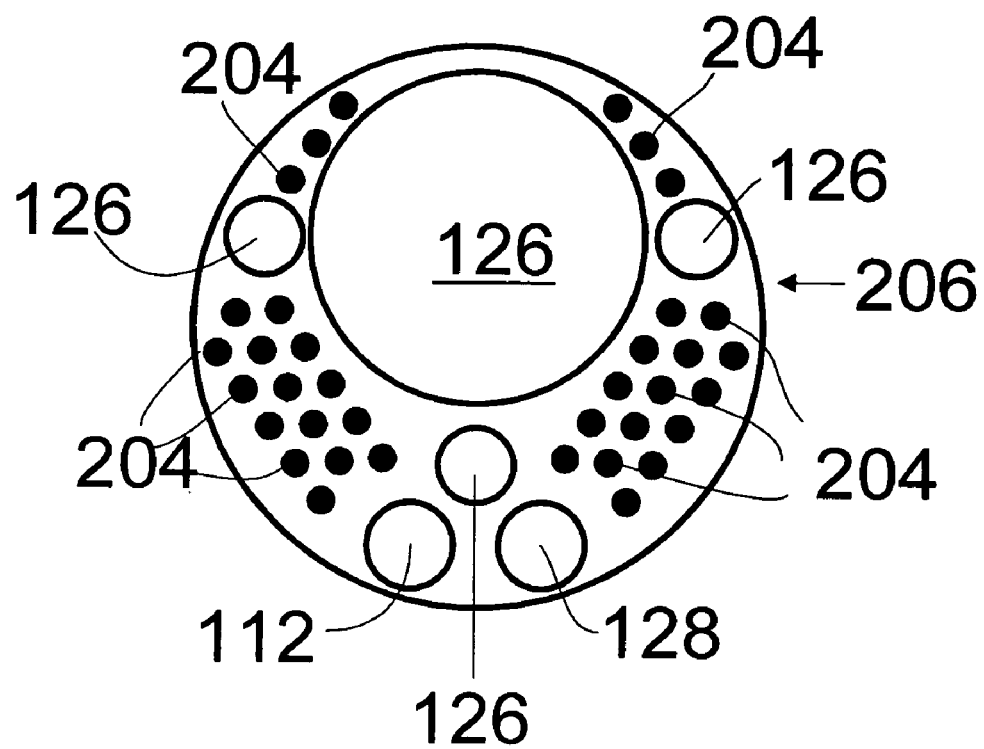
FIG. 38 is a cross-sectional view of an EndoFiber in accordance with one embodiment.
Figure 39:
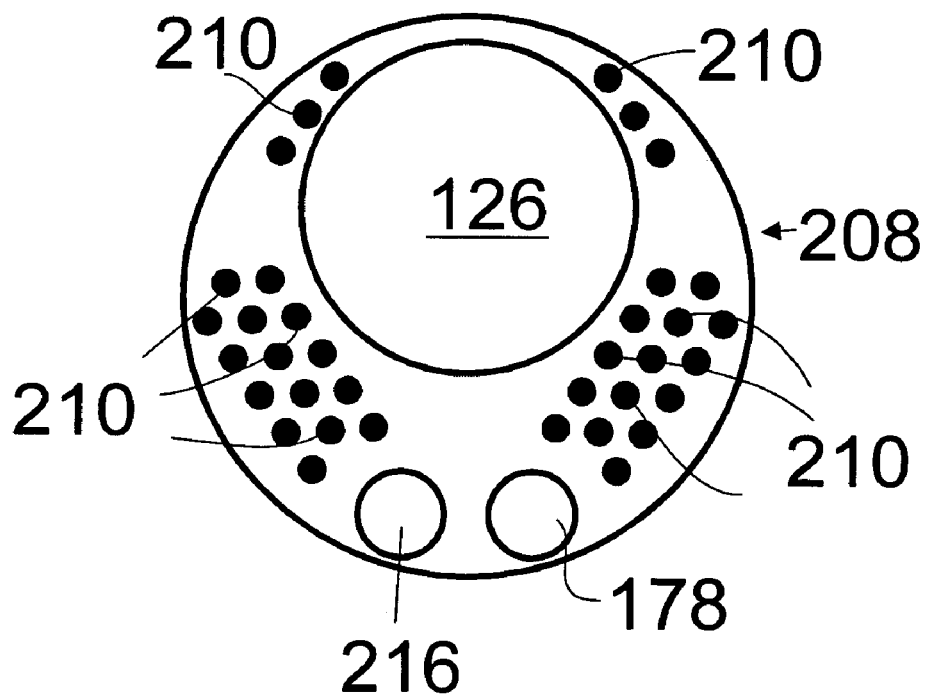
FIG. 39 is a top view of an EndoCap in accordance with one embodiment.

In one embodiment of the present invention the EndoFiber 206 has a cross section as shown in FIG. 38, wherein are contained three articulation lumens 126, one therapeutic lumen 126, one light guide 128, one imaging guide 112 and a plurality of additional light guides and or sensing/detecting guides 204. The EndoCap 208 is shown in cross section in FIG. 39. The EndoCap contains the same elements as the EndoFiber in FIG. 38 with the exception that the imaging guides and light guides are replaced by optical elements that manipulate the direction and/or focus/defocus the light along with replacing some or all of the light guides and or sensing/detecting guides 204 with more sensing/detecting guides 210.

The use of EndoFibers makes it physically possible and economically feasible to incorporate a number of different features and functionalities into an endoscope. The foregoing are examples of a few of such features. The manufacturing process is very flexible—it may combine, separate out, or rearrange any of the elements and/or features of the EndoFibers. Additional examples are provided in the following paragraphs.

During some procedures the position of the endoscope's distal end is verified by taking an X-ray. While endoscopic tools are generally radio opaque (i.e., show up in x-ray images), it is beneficial to have the endoscope shaft also be visible in an X-ray. In accordance with an embodiment, the polymer material in an EndoFiber endoscope shaft is doped with a material to increase its X-ray signature. For example, the common housing material may be doped with Barium compounds. Alternatively, doped rods may be included in the preform.

Fluorescence and reflectance probes have gathered much attention lately as a way to detect cancer and other abnormalities in the body. This is often referred to as optical biopsy. The basic principle of operation is that healthy tissue exhibits different fluorescence and reflectance than unhealthy tissue. Sometimes chemicals are introduced into the tissue to create/enhance this difference. While this technology is still very early in its development, it is starting to make an appearance in commercial products. Olympus has introduced a probe that may detect "suspicious tissue" in the lungs. The present invention will help bring such an endoscope to market by making the probes inexpensive and disposable. Essentially these probes are composed of "supply" light guides and "receive" light guides. In more advanced designs both of the supply and receive light guides must be precisely physically arranged in complex patterns such that the optical information about the tissue being examined may be deconvoluted.

Sensors having both sensor and imaging abilities (as combined in an EndoFiber) are useful elsewhere as well. For instance, the combination of an imaging guide and a cancer sensor will allow a doctor to both give a confident prognosis and a visual confirmation of the condition, all without performing a standard biopsy and ordering expensive laboratory tests.

Many dyes have been investigated for use with fiber optic sensors. A common method is to coat the end of a glass optical fiber with the dye substance, insert this coated end into the body, and measure changes in the dye's absorption or some other optical characteristic. Coating the end of the fiber is an expensive and time-consuming process. In accordance with an embodiment, such dyes are incorporated into the polymer that is used to form the EndoFiber and/or EndoCap. Incorporating the dye into the polymer itself (and then into EndoFiber or EndoCaps) provides a cost-effective and quick method for detecting various conditions.

Two readily available dyes are: Nile Red and (tris) Ruthenium TMHD. Nile Red has been examined for use with fiber optic probes to detect organic vapors. Ruthenium complexes have been examined for use with fiber optic sensors to detect cholesterol levels. Chelating the ruthenium allows the metal to be introduced into the polymer matrix.

In addition to the aforementioned dyes there are several other applications with dye-sensor mechanisms. The list includes sensors for TNT, blood gas levels, pesticides, ammonia, and heavy metals. Other examples are sensors for physiological pH levels and oxygen gradients in engineered tissue.

By incorporating the dye into the polymer itself (and then into EndoFiber or EndoCaps), the more costly dye/glass fiber sensor combination is replaced with an inexpensive, easily fabricated EndoFiber and/or EndoCap. For example, Pringsheim et. al. have used polymer beads infused with dyes to sense pH levels in the physiological range. The polymer beads are then placed in the etched cores of a glass imaging fiber and characterized. This process is expensive. The entire process is vastly simplified by the present embodiment, wherein the dye(s) are incorporated into a polymer and the polymer is drawn into imaging fiber form.

Other variations are within the spirit of the present invention. Thus, while the invention is susceptible to various modifications and alternative constructions, a certain illustrated embodiment thereof is shown in the drawings and has been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein may be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of forming an endoscopic shaft, comprising:
    combining a polymer common housing and at least one drawable endoscopic element to form a preform such that said polymer common housing is below its glass transition temperature when in the preform;
    drawing the preform to form a fiber;
    removing a length of the fiber, the length of the fiber having a distal end; and
    connecting at least one distal endoscopic element to the distal end.

2. The method of claim 1, wherein non-drawable material is pulled into the polymer common housing during the drawing of the preform.

3. The method of claim 2, further comprising:
    prior to pulling the non-drawable material into the common housing, coating the non-drawable material with a coating material; and
    removing the coating material after drawing of the preform.

4. The method of claim 1, wherein said at least one drawable endoscopic element is a subset of source light channels, laser light channels, imaging guides, and active and sensing fibers.

5. The method of claim 4, wherein non-drawable material is pulled into the polymer common housing during the drawing of the preform.

6. The method of claim 5, further comprising:
    prior to pulling the non-drawable material into the common housing, coating the non-drawable material with a coating material; and
    removing the coating material after drawing of the preform.

7. The method of claim 1, further comprising heating the preform prior to drawing.

8. The method of claim 1, wherein the preform defines an interior channel configured such that drawing the preform forms the interior channel into a lengthwise lumen.

9. The method of claim 1, wherein said at least one endoscopic element includes an outer lateral surface, substantially all of which is in contact with the polymer common housing.

10. The method of claim 1, wherein said at least one drawable endoscopic element includes a polymer endoscopic element.

11. The method of claim 1, including attaching a cap to a distal end of the endoscopic shaft.

12. The method of claim 1, wherein drawing the preform to form the endoscopic shaft includes drawing an articulation wire into the endoscopic shaft such that the articulation wire is coated with a removable material when in the endoscopic shaft.

13. The method of claim 1, wherein said at least one drawable endoscopic element includes a light guide and wherein drawing the preform to form the endoscopic shaft includes:
    drawing an articulation wire into the endoscopic shaft; and
    drawing the endoscopic shaft to a diameter of less than 250 microns.

14. The method of claim 1, wherein said at least one distal endoscopic element includes at least one endoscopic cap.

15. The method of claim 14, wherein said at least one endoscopic cap includes at least one optical element.

16. The method of claim 15, wherein the length of the fiber includes a plurality of imaging guides;
    wherein said at least one optical element includes a plurality of optical elements corresponding to the plurality of imaging guides; and
    wherein said connecting includes connecting the length of the fiber to said at least one endoscopic cap such that the plurality of optical elements transmits light from a plurality of directions to corresponding imaging guides.

17. The method of claim 15, wherein the length of the fiber includes a plurality of imaging guides;
    wherein said at least one optical element includes a plurality of optical elements corresponding to the plurality of imaging guides, each of the plurality of optical elements having a common focal point; and
    wherein said connecting includes connecting the length of the fiber to said at least one endoscopic cap such that the plurality of optical elements transmits light to corresponding imaging guides.

18. The method of claim 1, wherein said distal endoscopic element includes at least one lens.

19. A method of forming an endoscopic shaft, comprising:
    combining a polymer common housing and at least one drawable endoscopic element to form a preform such that said polymer common housing is below its glass transition temperature when in the preform;
    heating the preform;
    drawing the preform to form a fiber;
    removing a length of the fiber, the length of the fiber having a distal end; and
    connecting at least one distal endoscopic element to the distal end.

20. The method of claim 19, wherein non-drawable material is pulled into the polymer common housing during the drawing of the preform.

21. The method of claim 20, further comprising:
   prior to pulling the non-drawable material into the common housing, coating the non-drawable material with a coating material; and
   removing the coating material after drawing of the preform.

22. The method of claim 19, wherein said at least one endoscopic element is a subset of source light channels, laser light channels, imaging guides, and active and sensing fibers.

23. The method of claim 22, wherein non-drawable material is pulled into the polymer common housing during the drawing of the preform.

24. The method of claim 23, further comprising:
   prior to pulling the non-drawable material into the common housing, coating the non-drawable material with a coating material; and
   removing the coating material after drawing of the preform.

25. The method of claim 19, wherein the preform defines at least one interior channel configured such that drawing the preform forms each of said at least one interior channel into a lengthwise lumen.

26. The method of claim 19, wherein said at least one endoscopic element includes an outer lateral surface, substantially all of which is in contact with the polymer common housing.

27. The method of claim 19, wherein said at least one drawable endoscopic element includes a polymer endoscopic element.

28. The method of claim 19, including attaching a cap to a distal end of the endoscopic shaft.

29. The method of claim 19, wherein drawing the preform to form the endoscopic shaft includes drawing an articulation wire into the endoscopic shaft such that the articulation wire is coated with a removable material when in the endoscopic shaft.

30. The method of claim 19, wherein said at least one distal endoscopic element includes at least one endoscopic cap.

31. The method of claim 30, wherein said at least one endoscopic cap includes at least one optical element.

32. The method of claim 31, wherein the length of the fiber includes a plurality of imaging guides;
   wherein said at least one optical element includes a plurality of optical elements corresponding to the plurality of imaging guides; and
   wherein said connecting includes connecting the length of the fiber to said at least one endoscopic cap such that the plurality of optical elements transmits light from a plurality of directions to corresponding imaging guides.

33. The method of claim 31, wherein the length of the fiber includes a plurality of imaging guides;
   wherein said at least one optical element includes a plurality of optical elements corresponding to the plurality of imaging guides, each of the plurality of optical elements having a common focal point; and
   wherein said connecting includes connecting the length of the fiber to said at least one endoscopic cap such that the plurality of optical elements transmits light to corresponding imaging guides.

34. The method of claim 19, wherein said distal endoscopic element includes at least one lens.

35. A method of forming an endoscopic shaft, comprising:
   combining a polymer common housing and at least one polymer endoscopic element to form a preform;
   drawing the preform; and
   pulling non-drawable material into the polymer common housing during the drawing of the preform.

36. The method of claim 35, further comprising:
   prior to pulling the non-drawable material into the common housing, coating the non-drawable material with a coating material; and
   removing the coating material after drawing of the platform.

37. The method of claim 35, wherein said at least one drawable endoscopic element includes a polymer endoscopic element.

38. A method of forming and using an endoscopic shaft, comprising:
   combining a polymer common housing and at least one drawable endoscopic element to form a preform such that said polymer common housing is below its glass transition temperature when in the preform; and
   drawing the preform to form an endoscopic shaft; and
   using the endoscopic shaft in an endoscopic procedure.

39. The method of claim 38, further comprising:
   wherein said at least one drawable endoscopic element is a subset of source light channels, laser light channels, imaging guides, and active and sensing fibers.

40. The method of claim 38, further comprising:
   forming a distal end of the endoscopic shaft;
   connecting a distal endoscopic element to the distal end.

41. The method of claim 40, wherein forming the distal end includes cutting the endoscopic shaft.

* * * * *